(12) United States Patent
Albrecht et al.

(10) Patent No.: US 8,382,707 B2
(45) Date of Patent: Feb. 26, 2013

(54) BALLOON TROCAR ADVANCED FIXATION

(75) Inventors: Jeremy J. Albrecht, Ladera Ranch, CA (US); Kevin K. Dang, Garden Grove, CA (US); Kennii Pravongviengkham, Garden Grove, CA (US)

(73) Assignee: Applied Medical Resources Corporation, Rancho Santa Margarita, CA (US)

( * ) Notice: Subject to any disclaimer, the term of this patent is extended or adjusted under 35 U.S.C. 154(b) by 726 days.

(21) Appl. No.: 12/396,624

(22) Filed: Mar. 3, 2009

(65) Prior Publication Data

US 2009/0221960 A1 Sep. 3, 2009

Related U.S. Application Data

(60) Provisional application No. 61/033,215, filed on Mar. 3, 2008.

(51) Int. Cl.
*A61M 29/00* (2006.01)

(52) U.S. Cl. .......... 604/101.01; 604/103.07; 604/164.02

(58) Field of Classification Search ............. 604/103.03, 604/96.01, 101.01, 101.03, 101.05, 102.01–102.03, 604/103.07, 104, 97.01, 158, 164.02–164.03
See application file for complete search history.

(56) References Cited

U.S. PATENT DOCUMENTS

| | | | |
|---|---|---|---|
| 2,687,131 A | 8/1954 | Raiche | |
| 3,039,468 A | 6/1962 | Price | |
| 3,154,077 A | 10/1964 | Cannon | |
| 3,253,594 A | 5/1966 | Matthews et al. | |
| 3,459,175 A | 8/1969 | Miller | |
| 3,952,742 A | 4/1976 | Taylor | |
| 4,077,412 A | 3/1978 | Moossum | |
| 5,147,316 A | 9/1992 | Castillenti | |
| 5,176,697 A | 1/1993 | Hasson et al. | |
| 5,290,249 A | 3/1994 | Foster et al. | |
| 5,331,975 A | 7/1994 | Bonutti | |
| 5,354,270 A | 10/1994 | Wilk et al. | |
| 5,445,615 A | 8/1995 | Yoon | |
| 5,540,675 A | 7/1996 | Hasson | |
| 5,634,937 A * | 6/1997 | Mollenauer et al. | 606/213 |
| 5,656,013 A | 8/1997 | Yoon | |
| 5,713,869 A | 2/1998 | Morejon | |
| 5,830,232 A | 11/1998 | Hasson | |
| 5,924,424 A | 7/1999 | Stevens et al. | |
| 5,951,588 A | 9/1999 | Moenning | |
| 6,102,928 A | 8/2000 | Bonutti | |
| 6,908,454 B2 | 6/2005 | McFarlane | |
| 7,052,454 B2 * | 5/2006 | Taylor | 600/114 |

(Continued)

OTHER PUBLICATIONS

Arthrex Inc., Fulfilling the Need for Precision & Speed in Arthroscopic Rotator Cuff Repair, advertisement brochure 2008.
Arthrex, Inc., A Technical Pearls Newsletter for Arthroscopists, Spring 2008, vol. 10, No. 1, pp. 1-8.
The International Bureau of WIPO, International Preliminary Report on Patentability for International Application No. PCT/US2009/035810, dated Sep. 7, 2010, entitled "Balloon Trocar Advanced Fixation".

(Continued)

*Primary Examiner* — Nicholas Lucchesi
*Assistant Examiner* — Melissa A Snyder
(74) *Attorney, Agent, or Firm* — John F. Heal

(57) ABSTRACT

A trocar cannula assembly can have a retention mechanism for advanced fixation. The retention mechanism can include a first, or distal balloon, and a second or proximal balloon to retain the position of the trocar cannula assembly with respect to a body wall of a patient. An inlet can be fluidly coupled to the retention mechanism via a fluid conduit so that the balloons can be selectively inflated and deflated. The retention mechanism can be coupled to the cannula, forming an integrated cannula assembly, or the retention mechanism can be removably attached to the cannula. Where the retention mechanism is removably attached to the cannula, it can include a double layer inflatable member with an outer layer including the first and second balloons, and an inner layer for retaining the cannula.

22 Claims, 34 Drawing Sheets

U.S. PATENT DOCUMENTS

| | | |
|---|---|---|
| 7,235,064 B2 | 6/2007 | Hopper et al. |
| 7,300,448 B2 | 11/2007 | Criscuolo et al. |
| 7,691,089 B2 | 4/2010 | Gresham |
| 2004/0116894 A1 | 6/2004 | DeLegge |
| 2004/0138702 A1 | 7/2004 | Peartree et al. |
| 2005/0165432 A1 | 7/2005 | Heinrich |
| 2006/0079838 A1 | 4/2006 | Walker et al. |
| 2007/0005086 A1* | 1/2007 | Gresham ............. 606/167 |
| 2007/0213675 A1* | 9/2007 | Albrecht et al. ............. 604/264 |
| 2007/0225643 A1* | 9/2007 | Hopper et al. ......... 604/101.01 |
| 2008/0306442 A1 | 12/2008 | Bardsley et al. |

OTHER PUBLICATIONS

European Patent Office, Extended European Search Report dated Jun. 16, 2011 for European Application No. EP 09 71 7684.

International Searching Authority/US, The International Search Report and Written Opinion for International Application No. PCT/US09/035810, mailed Apr. 15, 2009, entitled "Balloon Trocar Advanced Fixation".

* cited by examiner

BALLOON TROCAR ADVANCED FIXATION

CROSS REFERENCE TO RELATED APPLICATIONS

This application claims the benefit of U.S. Provisional Patent Application Ser. No. 61/033,215, entitled BALLOON TROCAR ADVANCED FIXATION, filed on Mar. 3, 2008, which is hereby incorporated herein by reference in its entirety.

BACKGROUND

1. Field

Trocar systems including cannulas and, more specifically, to trocars having a balloon retention device are provided. Trocar systems facilitate minimally invasive surgery across a body wall and within a body cavity. For example, in abdominal surgery, trocars provide a working channel across the abdominal wall to facilitate the use of instruments within the abdominal cavity.

2. Discussion of the Relevant Art

Trocar systems typically include a cannula, which provides the working channel, and an obturator that is used to place the cannula across a body wall, such as the abdominal wall. The obturator is inserted into the working channel of the cannula and pushed through the body wall with a penetration force of sufficient magnitude to result in penetration of the body wall. Alternatively, the cannula with an obturator is passed through an incision formed by the "Hassan," or cut-down, technique, which includes incremental incisions through the body wall until the body wall is incised through its entire thickness. Once the cannula has traversed the body wall, the obturator can be removed.

With the cannula in place in the body wall, various instruments may be inserted through the cannula into the body cavity. One or more cannulas may be used during a procedure. During the procedure, the surgeon manipulates the instruments in the cannulas, sometimes using more than one instrument at a time. The manipulation of an instrument by a surgeon may cause frictional forces between the instrument and the cannula in which the instrument is inserted. These frictional forces may result in movement of the cannula in an inward or outward direction within the body wall. If the cannula is not fixed in place, the proximal or distal motions of the instruments through the cannula may potentially cause the cannula to slip out of the body wall or to protrude further into the body cavity, possibly leading to injury to the patient.

The surfaces of the cannula associated with a trocar are generally smooth. The smoothness of a cannula surface makes placement of the cannula through a body wall relatively easy and safe. However, a smooth cannula may not have the desired retention characteristics once the cannula has been placed through a body wall. This may present problems as instruments and specimens are removed from a body cavity through the cannula and the associated seal systems of the trocar. It is highly desirable for a cannula to remain fixed in the most appropriate position once placed. Additionally, if the Hassan technique is used, the incision may be larger than the cannula that may be placed through the incision. Therefore, it can be desirable to provide a means to seal the incision site after the cannula has been inserted in order to insufflate a patient.

Many solutions to the issue of trocar-cannula fixation or stabilization have been formed. These solutions include an inflatable balloon attached to the distal portion of the cannula with a thick foam bolster proximal to the insertion point into the body wall, raised threads or raised rings associated with the outer surface of the cannula, mechanically deployable enlarging portions arranged at the distal end of a cannula and suture loops or hooks associated with the proximal end of the trocar. These solutions have provided some degree of fixation or stabilization, but they have often led to cannulas having a larger outside diameter. Further, the thick foam bolster associated with balloon trocars has reduced the usable length of the cannula.

Some prior art balloon trocars include a natural rubber latex balloon. Common laparoscopic surgeries may take up to four hours. The natural rubber latex balloons provide adequate air retention, thereby permitting proper balloon inflation during such a surgical procedure. However, many people are sensitive to latex and may be allergic to the balloon on the trocar. To accommodate those patients with allergies to latex, some prior art balloon trocars have the latex balloon coated with another material, such as silicone. The silicone coating reduces the likelihood of the patient being contacted by the latex. However, the silicone coating adds material thickness to the device, thereby increasing the outer profile of the device. Also, the patient may still be exposed to latex if the balloon ruptures or breaks during the surgical procedure.

There remains a need for a cannula fixation or stabilization device that maintains the position of the cannula with respect to the body wall of the patient. Additionally, the cannula fixation or stabilization device may be removably attachable to the cannula.

SUMMARY

In some embodiments a cannula assembly is provided comprising a cannula, a retention mechanism, an inlet, and a fluid conduit. The cannula has a proximal end, a distal end, an outer surface, and a lumen extending between the proximal end and the distal end. The lumen is adapted to receive a medical instrument therein. The retention mechanism is attached to the outer surface of the cannula and has a proximal end and a distal end. The retention mechanism comprises a first inflatable balloon, a second inflatable balloon, and a mid-section. The first inflatable balloon is positioned near the distal end of the retention mechanism. The second inflatable balloon is positioned between the proximal end and the distal end of the retention mechanism. The mid-section extends between the first inflatable balloon and the second inflatable balloon. The mid-section has an outer surface adapted to contact a body wall of a patient when in use. The inlet is near the proximal end of the retention mechanism. The inlet is in fluid communication with the first and second balloons and the mid-section of the retention mechanism. The fluid conduit fluidly couples the inlet with the first and second inflatable balloons. The mid-section is configured such that upon application of an inflation fluid to the inlet, the first and second balloons inflate before the mid-section.

In certain embodiments of the afore-described cannula assembly, at least one of the first and second balloons comprises a toroidal profile. In certain embodiments, both of the first and second balloons comprise a toroidal profile. In certain embodiments, at least one of the first and second balloons comprises a disc profile. In certain embodiments, both of the first and second balloons comprise a disc profile. In some embodiments, the fluid conduit comprises: an air inlet cavity fluidly coupled to the inlet; and a fluid channel extending generally longitudinally along the outer surface of the cannula. In certain embodiments, the inlet is integrally formed with the cannula. In certain embodiments, the retention mechanism is attached to the cannula by a proximal thread winding at the proximal end of the retention mechanism and a distal thread winding at the distal end of the retention mechanism.

In certain embodiments of the afore-described cannula assembly, the retention mechanism comprises a double layered balloon comprising: an inner balloon layer adapted to be slidably advanced over the cannula; and an outer balloon layer having the first inflatable balloon and the second inflatable balloon formed thereon; and the fluid conduit comprises a fluid chamber defined between the inner balloon layer and the outer balloon layer. In certain embodiments, the inner balloon layer comprises a cannula retention surface configured to retain the cannula. In certain embodiments, the cannula retention surface comprises an inner balloon inflatable to retain the outer surface of the cannula. In some embodiments, the cannula assembly further comprises an inlet housing coupled to the proximal end of the retention mechanism, and wherein the inlet is formed in the inlet housing.

In certain embodiments, a retention mechanism for a cannula assembly is provided comprising an inlet housing and an inflatable member. The inlet housing comprises an annular member and an inlet port. The annular member has an opening adapted to receive the cannula assembly. The inlet port is adapted to receive a source of inflation fluid. The inflatable member has a proximal end and a distal end. The proximal end of the inflatable member is fluidly coupled to the inlet port of the inlet housing. The inflatable member comprises an inner layer, an outer layer, and a fluid chamber. The inner layer defines a generally cylindrical surface adapted to receive the cannula assembly therein. The outer layer comprises a first inflatable projection and a second inflatable projection. The first inflatable projection is positioned near the distal end of the inflatable member. The second inflatable projection is positioned between the proximal end and the distal end of the inflatable member and spaced apart from the first inflatable projection. The fluid chamber is formed between the inner layer and the outer layer and is fluidly coupled to the inlet port.

In certain embodiments of retention mechanism, the inner layer of the inflatable member comprises a retention feature extending radially inwardly therefrom and configured to retain the cannula assembly. In certain embodiments, the retention feature comprises an inflatable balloon. In certain embodiments, the first inflatable projection and the second inflatable projections each comprise an inflatable balloon. In certain embodiments, the inflatable projection and the second inflatable projections each define a generally annular structure in an inflated state. In certain embodiments, the inlet port of the inlet housing is coupled to the annular member, and the annular member comprises fluid conduits fluidly coupled to the inlet port and fluidly coupled to the inflatable member. In certain embodiments, the inlet housing comprises a rigid material.

In certain embodiments, a cannula assembly is provided comprising a cannula and a retention mechanism. The cannula has a proximal end, a distal end, an outer surface, and a lumen extending between the proximal end and the distal end. The lumen is adapted to receive a medical instrument therein. The cannula comprises an inlet port and a fluid conduit. The inlet port is on the outer surface of the cannula. The fluid conduit extends generally longitudinally in the outer surface of the cannula. The fluid conduit is fluidly coupled to the inlet port. The retention mechanism is coupled to the outer surface of the cannula. The retention mechanism has a proximal end and a distal end. The retention mechanism comprises a first inflatable balloon and a second inflatable balloon. The first inflatable balloon is positioned near the distal end of the retention mechanism. The second inflatable balloon is positioned between the proximal end and the distal end of the retention mechanism. The first and second inflatable balloons are fluidly coupled to the fluid conduit on the cannula.

In certain embodiments of cannula assembly, the cannula further comprises an inlet dome formed on the outer surface thereof, the inlet dome defining an inlet chamber fluidly coupled to the inlet port and the fluid conduit. In certain embodiments, the inlet port comprises a check valve positioned therein, the check valve adapted to receive a syringe of fluid. In certain embodiments, the cannula further comprises a proximal groove and a distal groove and the retention mechanism further comprises a proximal thread winding at the proximal end of the retention mechanism and a distal thread winding at the distal end of the retention mechanism, the proximal thread winding coupling the retention mechanism to the proximal groove, and the distal thread winding coupling the retention mechanism to the distal groove. In certain embodiments, the first and second inflatable balloons each comprise a generally annular balloon. In certain embodiments, the second inflatable balloon has a smaller inflated volume than the first inflatable balloon.

In certain embodiments, a method of securing a cannula assembly for a laparoscopic procedure on a patient comprises providing a cannula assembly, inserting the cannula assembly into an incision in the patient, and inflating balloons on the cannula assembly. The cannula assembly comprises a cannula, a retention mechanism, an inlet, and a fluid conduit. The cannula has a proximal end, a distal end, an outer surface, and a lumen extending between the proximal end and the distal end. The lumen is adapted to receive a medical instrument therein. The retention mechanism is attached to the outer surface of the cannula and has a proximal end and a distal end. The retention mechanism comprises a first inflatable balloon, a second inflatable balloon, and a mid-section. The first inflatable balloon is positioned near the distal end of the retention mechanism. The second inflatable balloon is positioned between the proximal end and the distal end of the retention mechanism. The mid-section extends between the first inflatable balloon and the second inflatable balloon. The mid-section has an outer surface adapted to contact a body wall of a patient when in use. The inlet is near the proximal end of the retention mechanism. The inlet is in fluid communication with the first and second balloons and the mid-section of the retention mechanism. The fluid conduit fluidly couples the inlet with the first and second inflatable balloons. The mid-section is configured such that upon application of an inflation fluid to the inlet, the first and second balloons inflate before the mid-section. Inserting the cannula assembly into an incision comprises inserting the cannula assembly into an incision in the patient until the first inflatable balloon is positioned in a body cavity of the patient and the second inflatable balloon is outside of the incision of the patient. Inflating balloons on the cannula assembly comprises inflating the first and second inflatable balloons.

In certain embodiments of the method, inflating the first and second inflatable balloons comprises introducing a source of inflation fluid to the inlet of the cannula assembly. In certain embodiments, the source of inflation fluid comprises a syringe of air. In certain embodiments, providing the cannula assembly further comprises attaching the retention mechanism to the outer surface of the cannula. In certain embodiments, attaching the retention mechanism to the outer surface of the cannula comprises slidably advancing the retention mechanism over the outer surface of the cannula.

DETAILED DESCRIPTION

Figure 1:
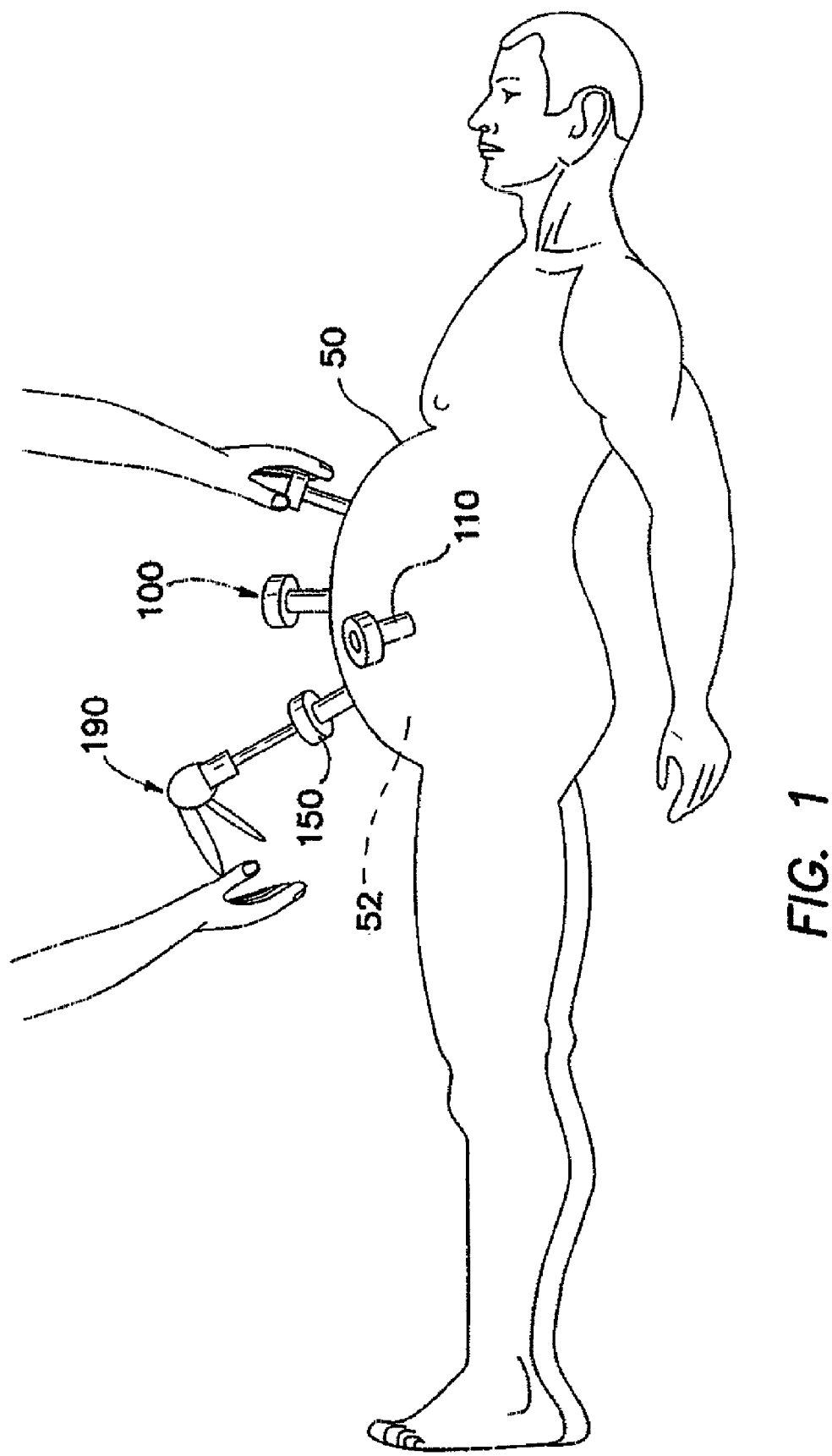
FIG. 1 is a side view of a laparoscopic surgical procedure.
Figure 2:
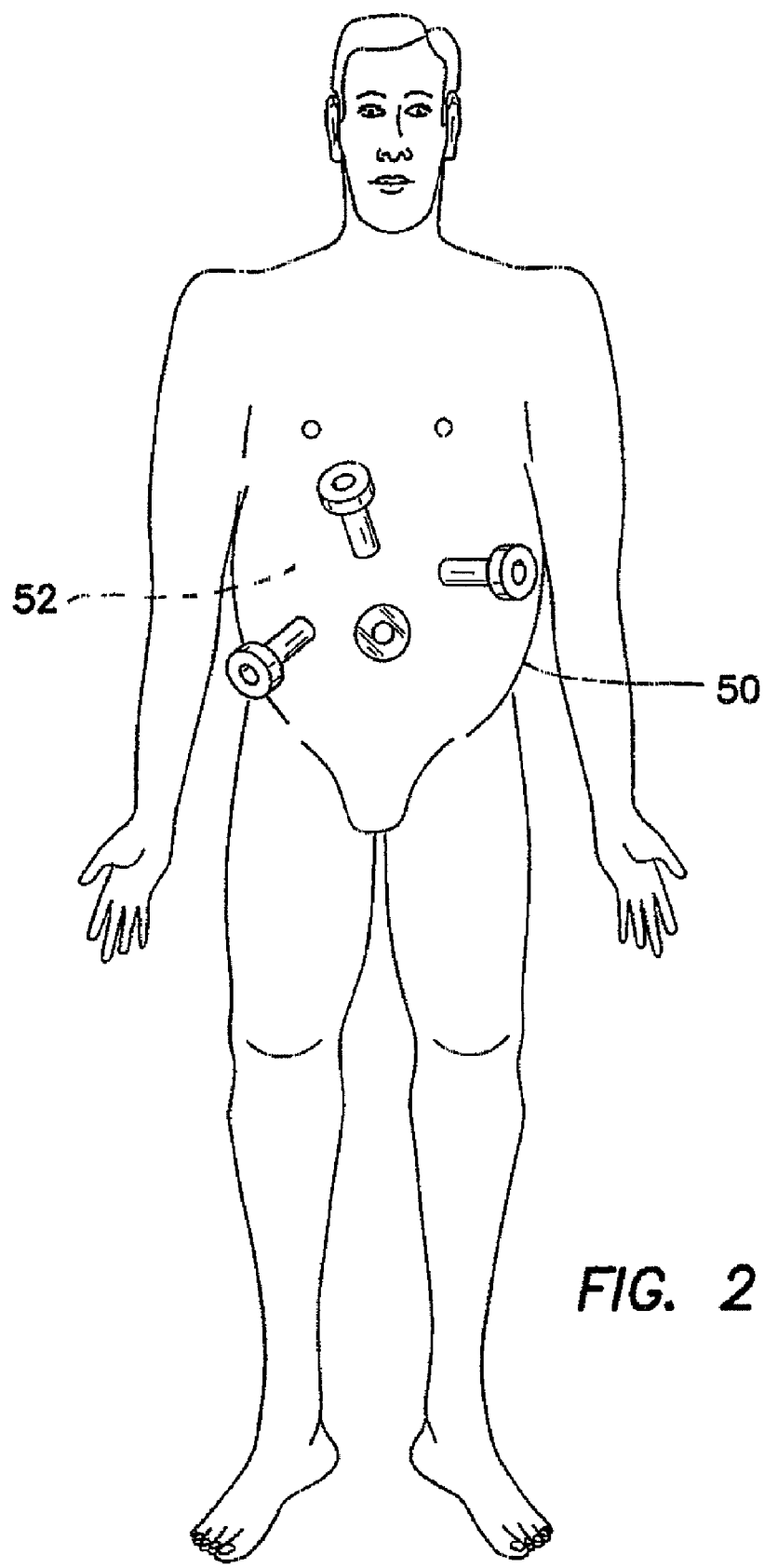
FIG. 2 is a plan view of a laparoscopic surgical procedure showing the placement of trocars.
Figure 5:
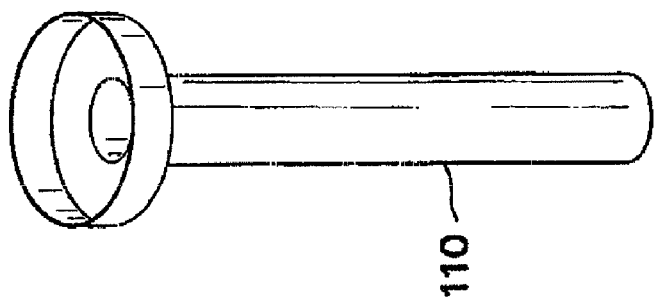
FIG. 5 is a perspective view of a prior art cannula.
Figure 4:
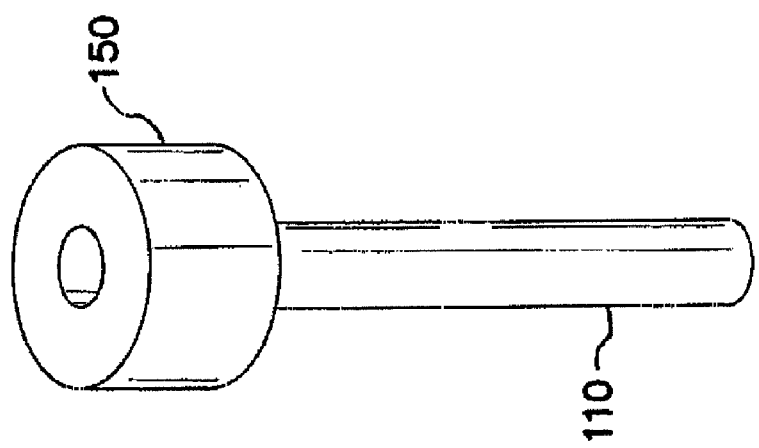
FIG. 4 is a perspective view of a prior art assembled trocar without an obturator.
Figure 3:
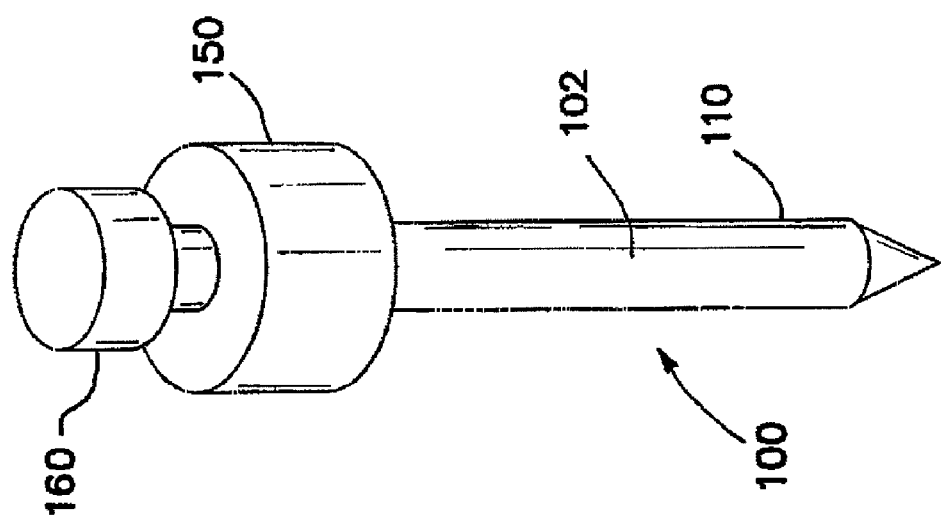
FIG. 3 is a perspective view of a prior art assembled trocar and obturator.

With reference to FIGS. 1 and 2, a typical laparoscopic procedure is illustrated where a plurality of trocars 100 are placed through a body wall 50, such as an abdominal wall, and into a body cavity 52, such as an abdominal cavity. The body cavity 52 is insufflated, or inflated with gas, to distend the body wall 50 and provide a working space for the laparoscopic procedure. The trocars 100 each include a cannula 110 and a seal 150. Positive pressure is maintained within the body cavity 52 by the seal 150 associated with the cannula 110. In addition, the cannula 110 must form a gas-tight seal against adjacent tissue. If positive pressure is lost, either through the seal 150 associated with the cannula 110 or the seal between the cannula and the adjacent tissue, the procedure may be compromised.

As the body cavity 52 is inflated, the body wall 50 may be greatly distended. The access sites may tend to enlarge under the distention of the body wall 50 and compromise the positioning and sealing of the cannula 110. As stated above, the manipulation of instruments 190 used through the trocars 100 may result in movement of the cannulas 110 in either a proximal or distal direction within the access site through the body wall 50. As this occurs, some liquefaction may take place and the preferred relationship between the cannula 110 and the body tissue may be compromised.

Referring now to FIGS. 3-6, a typical assembled trocar 100 is shown having a cannula 110, a seal housing 150 and an obturator 160. The cannula 110 typically has a smooth exterior surface 102 so that it may be inserted through the body wall 50 easily. The seal housing 150 contains a seal system that prevents retrograde gas-flow. The obturator 160 is a cutting or piercing instrument that creates the pathway through the body wall 50 through which the cannula 110 follows. Surgical obturators 160 are generally sized and configured to create a defect in tissue that is appropriate for the associated cannula 110. However, the defect may have a tendency to enlarge during a surgical procedure as the trocar 100 or cannula 110 is manipulated. As an instrument 190 is urged distally and proximally, or inserted and withdrawn, the cannula 110 may move or even be inadvertently withdrawn due to the friction between the instrument 190 and the seal 150 of the trocar housing.

Figure 8:
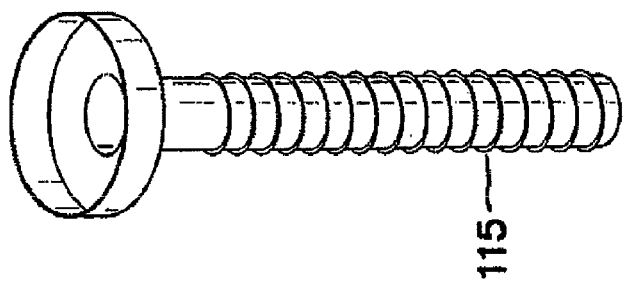
FIG. 8 is a perspective view of a prior art threaded cannula.
Figure 7:
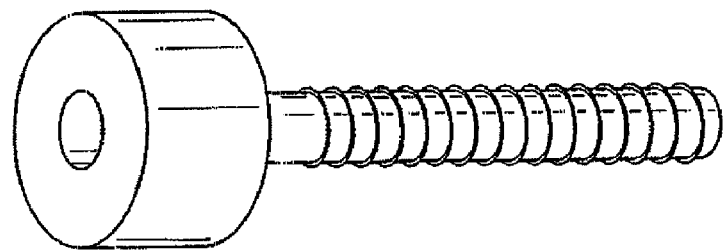
FIG. 7 is a perspective view of a prior art threaded cannula and housing.
Figure 6:
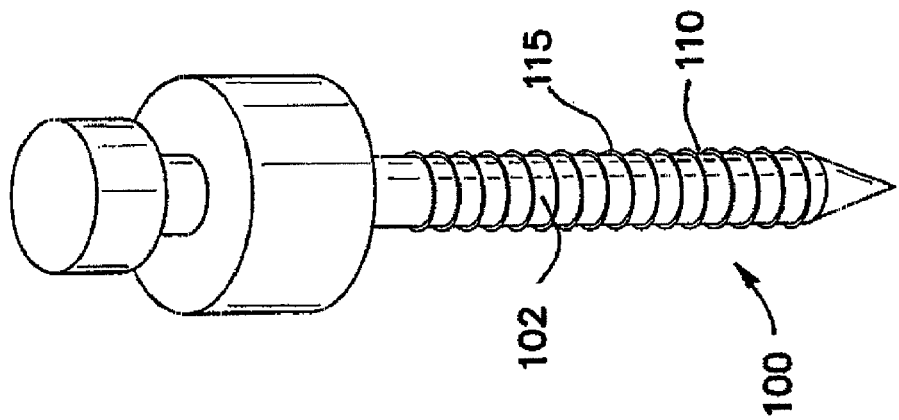
FIG. 6 is a perspective view of a prior art assembled threaded trocar and obturator.
Figures 9, 10:
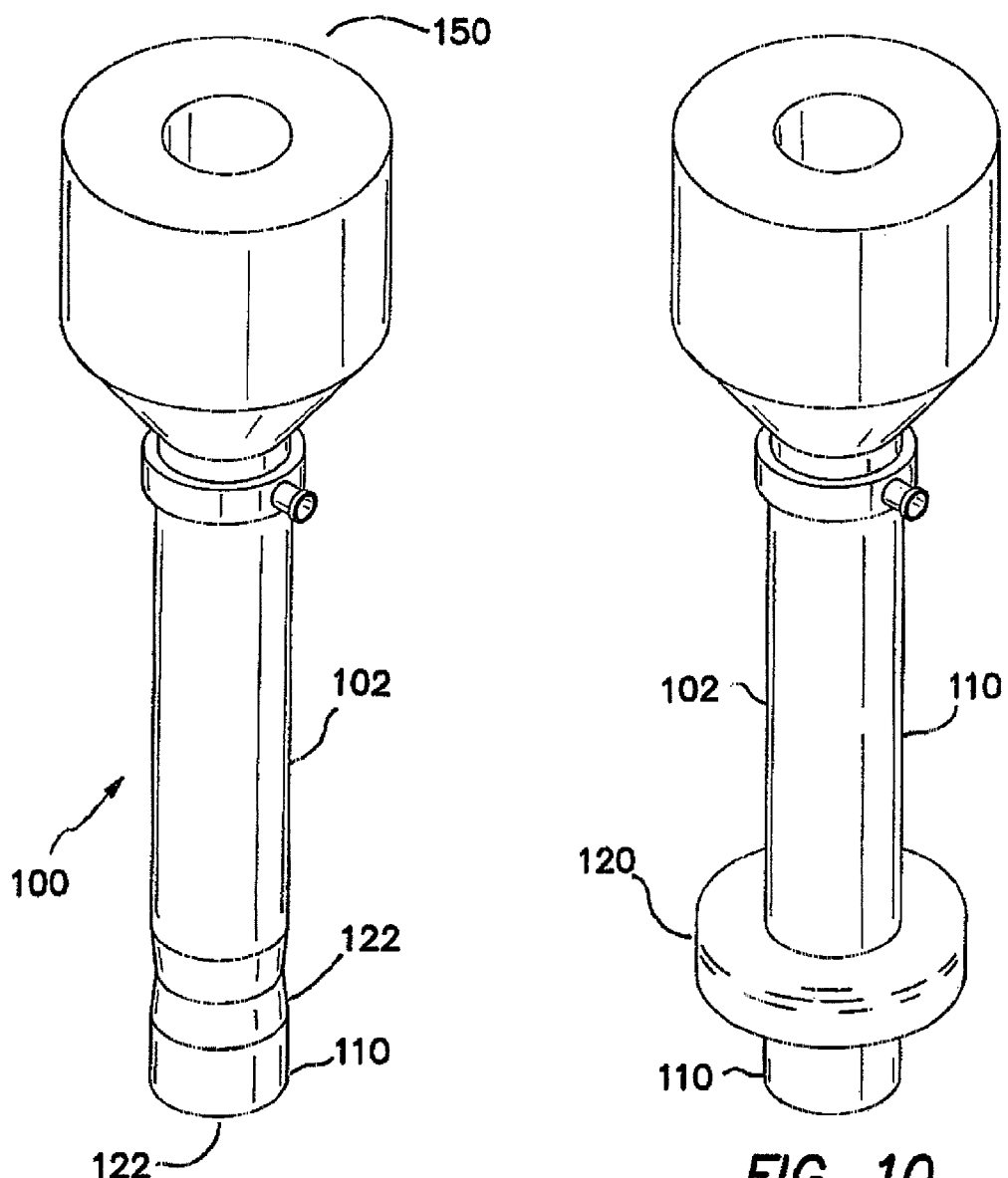
FIG. 9 is a perspective view of a prior art cannula having an uninflated balloon at the distal end.
FIG. 10 is a perspective view of a prior art cannula having an inflated balloon at the distal end.
Figure 11:
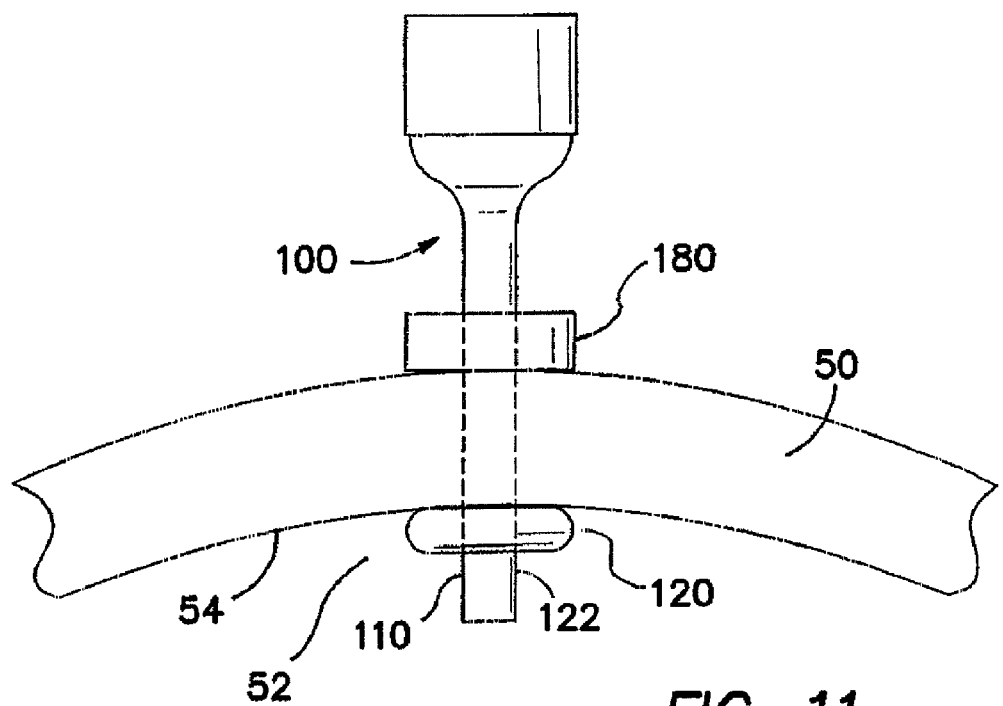
FIG. 11 illustrates a prior art trocar-cannula having a distal retention balloon placed through a body wall in a first position.
Figure 12:
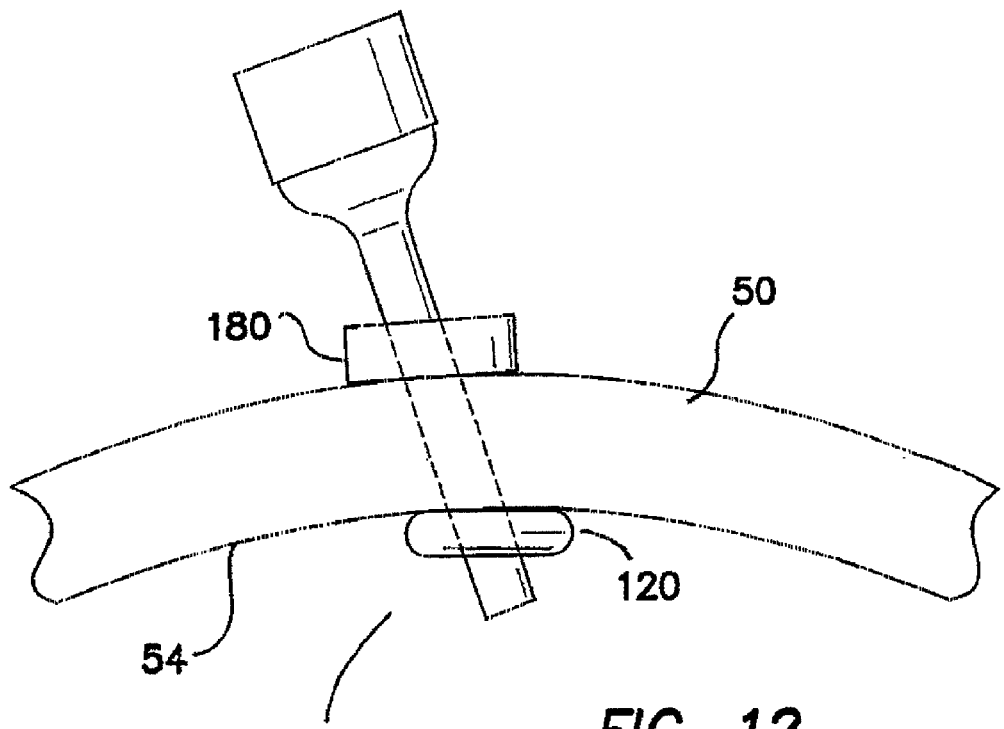
FIG. 12 illustrates a prior art trocar-cannula having a distal retention balloon placed through a body wall in a second position.

With specific reference to FIGS. 6-8, a trocar 100 or access device is shown where the outer surface 102 of the cannula 110 includes a plurality of raised features 115. These raised features 115 are sized and configured to increase resistance to proximal and distal motion as instruments 190 are maneuvered, and especially as specimens are removed, through the trocar 100. The prior art includes either sequential raised rings or a raised coarse-thread 115. While the rings or threads 115 of the prior art may stabilize the cannula 110 to some degree, they do not necessarily seal the cannula 110 against the adjacent tissue of a body wall 50. There may be gas loss associated with the use of these systems. The raised rings or threads 115 also increase the insertion force required to penetrate a body wall 50. The insertion force may be reduced in the instance of a continuous coarse thread 115 in comparison to a sequence of discrete raised rings or features as a threaded cannula 110 may actually be "screwed" into the tissue defect in accordance with the thread direction and pitch, rather than pushed through without appropriate rotation.

Figure 13:
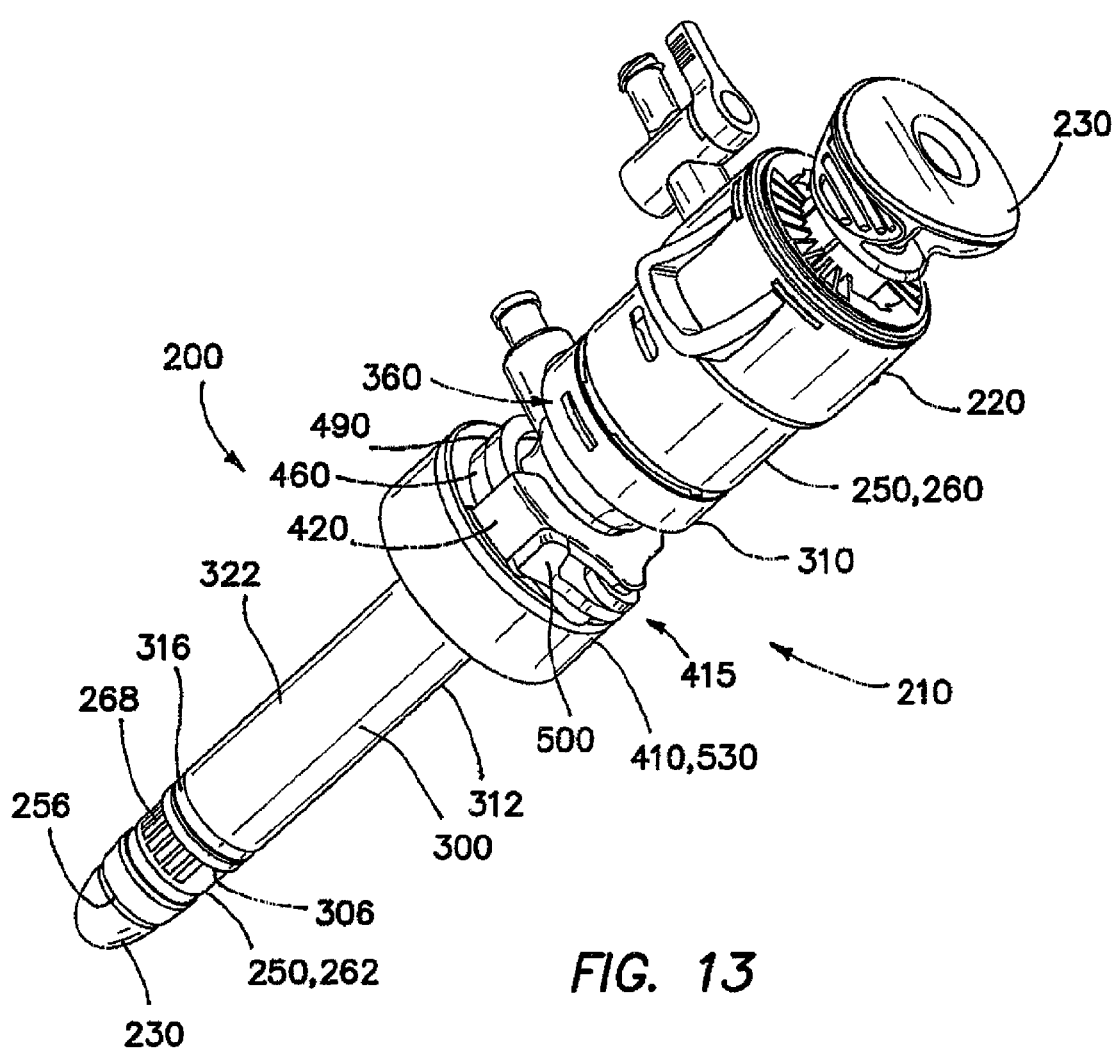
FIG. 13 is a perspective view of a balloon trocar having a bolster.

With reference to FIGS. 9-12, a surgical access device 100 according to prior art includes a cannula 110 having an inflatable balloon 120 associated with the distal-end portion 122 of the cannula. The balloon 120 is sized and configured to fit snugly around the cannula 110 in the uninflated condition. The balloon 120 is inflated after the cannula 110 is properly placed through the body wall 50 and into the body cavity 52. The balloon 120 is generally held against the interior surface 54 of the body wall 50 by a counter-force that is associated with a sliding counter-force member, such as a foam bolster 180. The bolster 180 is associated with the proximal portion of the cannula 110. The balloons 120 associated with the devices of the prior art are typically "thick-walled" structures constructed as part of the cannula 110. The balloon 120 is generally bonded to the distal-end portion 122 of the cannula 110 and an inflation channel or lumen is provided within the wall of the cannula 110. Referring to FIG. 13, one aspect of the balloon trocar 200 includes a cannula assembly 210, a trocar seal 220 and an obturator 230. The cannula assembly 210 includes a cannula 250 and an outer sleeve 300.

Figure 14:
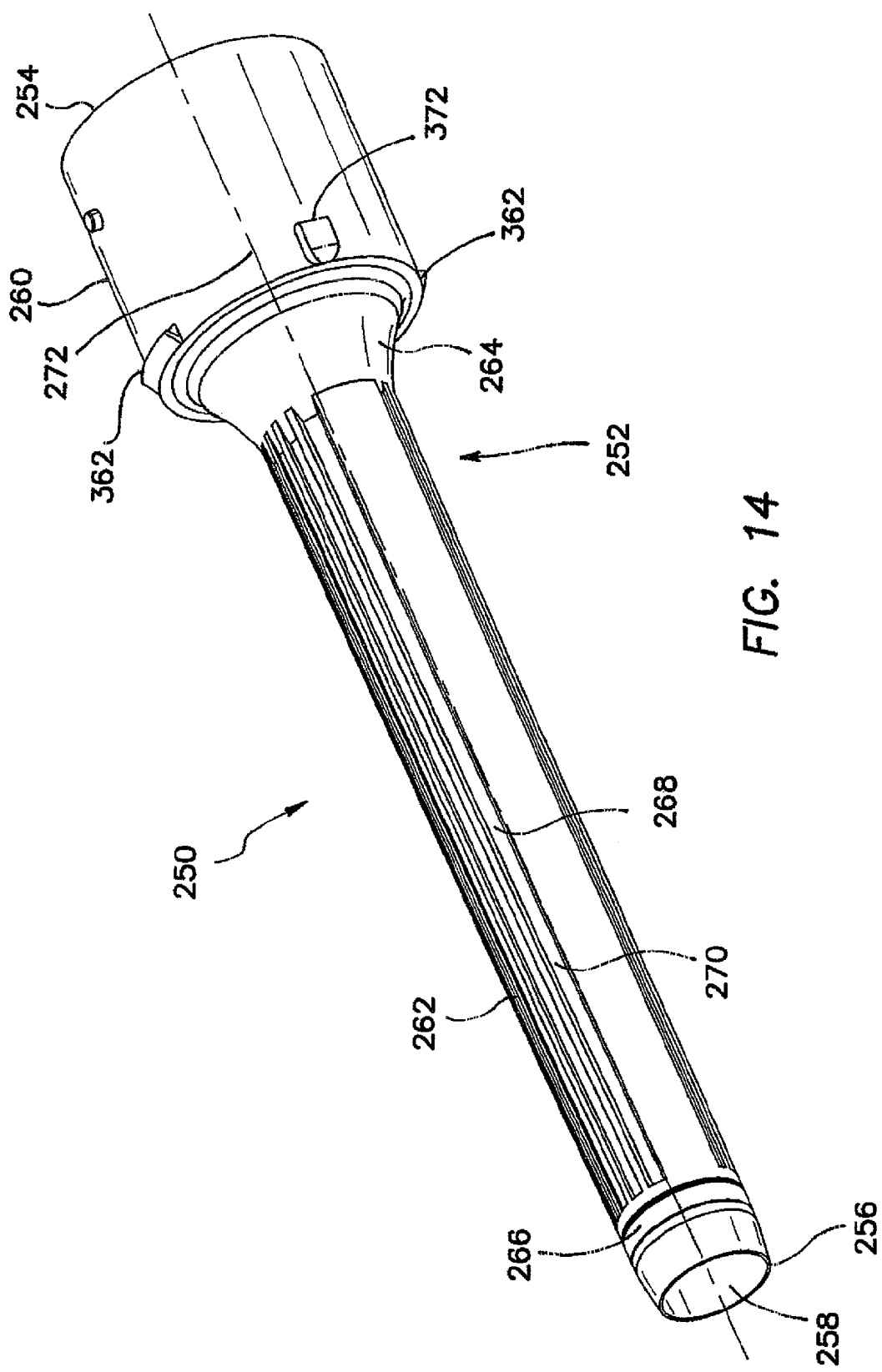
FIG. 14 is a perspective view of a cannula portion of the balloon trocar of FIG. 13.

Referring to FIG. 14, the cannula 250 includes a substantially longitudinal tube 252 having a proximal end 254, a distal end 256, and a lumen 258 therebetween. The cannula 250 may include at least a proximal portion 260 having a first, larger periphery and a distal portion 262 having a second, smaller periphery. In one aspect, the proximal portion 260 and distal portion 262 of the cannula 250 may each include a substantially cylindrical portion, with the proximal portion 260 having a first, larger circumference and the distal portion 262 having a second, smaller circumference. The cannula 250 may also include a transition region 264 between the proximal portion 260 and the distal portion 262. The lumen 258 of the cannula 250 may be substantially smooth and configured to accept the obturator 230 (see FIG. 13). The proximal portion 260 of the cannula 250 may be configured to accept the trocar seal 220 (see FIG. 13). The outer surface of the distal portion 262 of the cannula 250 includes an annular groove 266 toward the distal end 256 of the distal portion of the cannula. The annular groove 266 may lie within a plane that is substantially perpendicular to a longitudinal axis 272 of the cannula 250. Additionally, the outer surface of the distal portion 262 of the cannula 250 includes a plurality of channels 268 extending along the length of the cannula from substantially the proximal end of the distal portion of the cannula distally to a point proximal to the annular groove 266 near the distal end 256 of the distal portion of the cannula. The plurality of channels 268 is adapted to facilitate the flow of gases or fluids therethrough. In one aspect, the plurality of channels 268 may include a plurality of substantially longitudinal grooves 270 that are substantially parallel to the longitudinal axis 272 of the cannula 250. In one aspect, the cannula 250 may be made of a polymeric material, such as a polycarbonate material.

Figure 15:
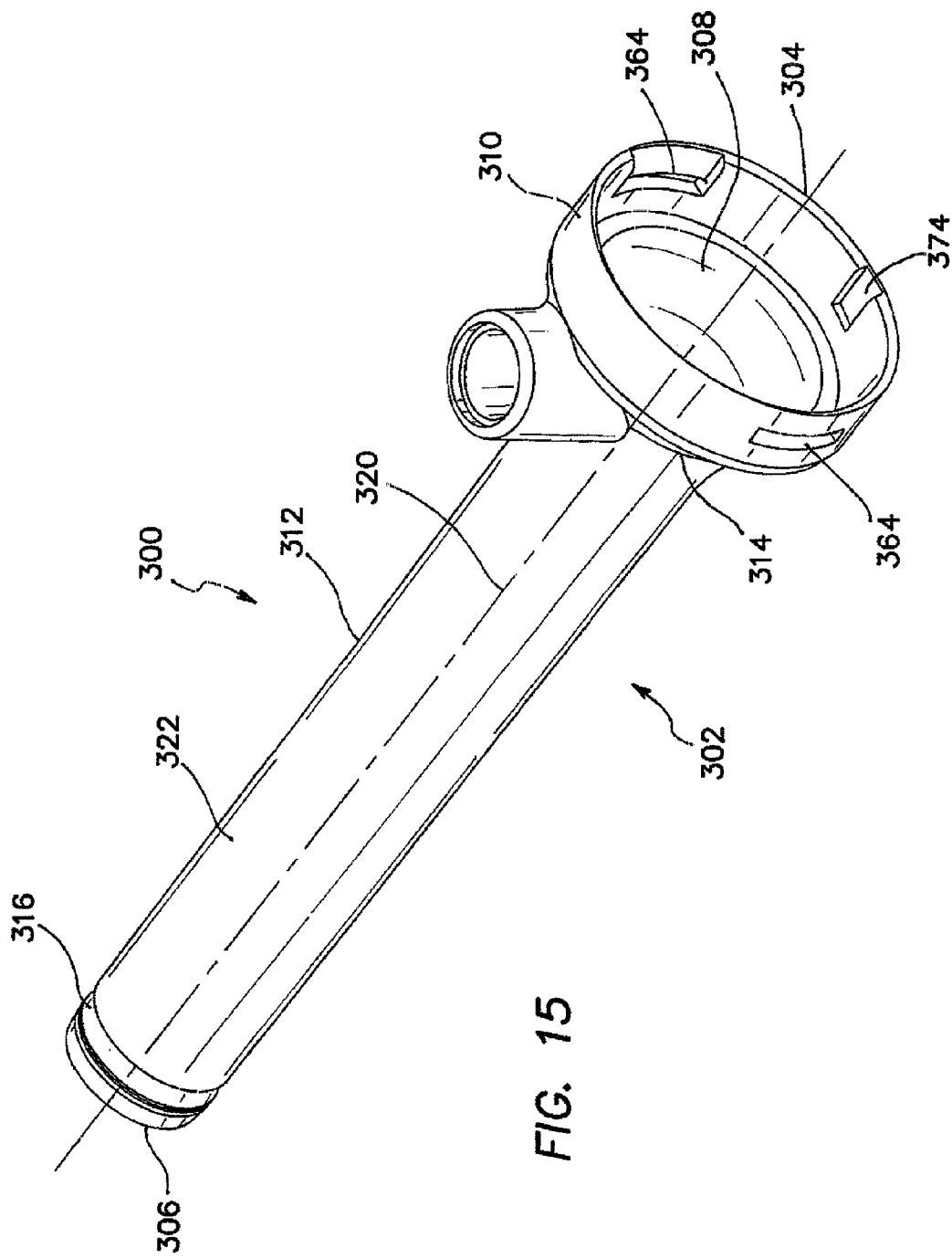
FIG. 15 is a perspective view of a sleeve portion of the balloon trocar of FIG. 13.

Referring to FIG. 15, the outer sleeve 300 of the cannula assembly 210 includes a substantially longitudinal tube 302 having a proximal end 304, a distal end 306, and a lumen 308 therebetween. The sleeve 300 may also include at least a proximal portion 310 having a first, larger periphery and a distal portion 312 having a second, smaller periphery. In one aspect, the proximal portion 310 and distal portion 312 of the sleeve 300 may each include a substantially cylindrical portion, with the proximal portion 310 having a first, larger circumference and the distal portion 312 having a second, smaller circumference. The sleeve 300 may include a transition region 314 between the proximal portion 310 and the distal portion 312. The lumen 308 of the sleeve 300 is configured to accept the cannula 250 (see FIG. 13) and may be substantially smooth. An outer surface 322 of the distal portion 312 of the sleeve 300 includes an annular groove 316 toward the distal end 306 of the distal portion of the sleeve. The annular groove 316 may lie within a plane that is substantially perpendicular to a longitudinal axis 320 of the sleeve 300. In one aspect, the sleeve 300 may be made of a polymeric material, such as a polycarbonate.

Referring again to FIG. 13, with the sleeve 300 positioned over the cannula 250, the proximal portion 310 of the sleeve 300 fits over at least a distal region of the proximal portion 260 of the cannula and the distal portion 312 of the sleeve fits over at least a portion of the distal portion 262 of the cannula. Additionally, with the sleeve 300 positioned over the cannula 250, the distal end 306 of the sleeve 300 is positioned proximal to a distal end of the plurality of channels 268 on the outer surface of the cannula 250.

Figure 16:
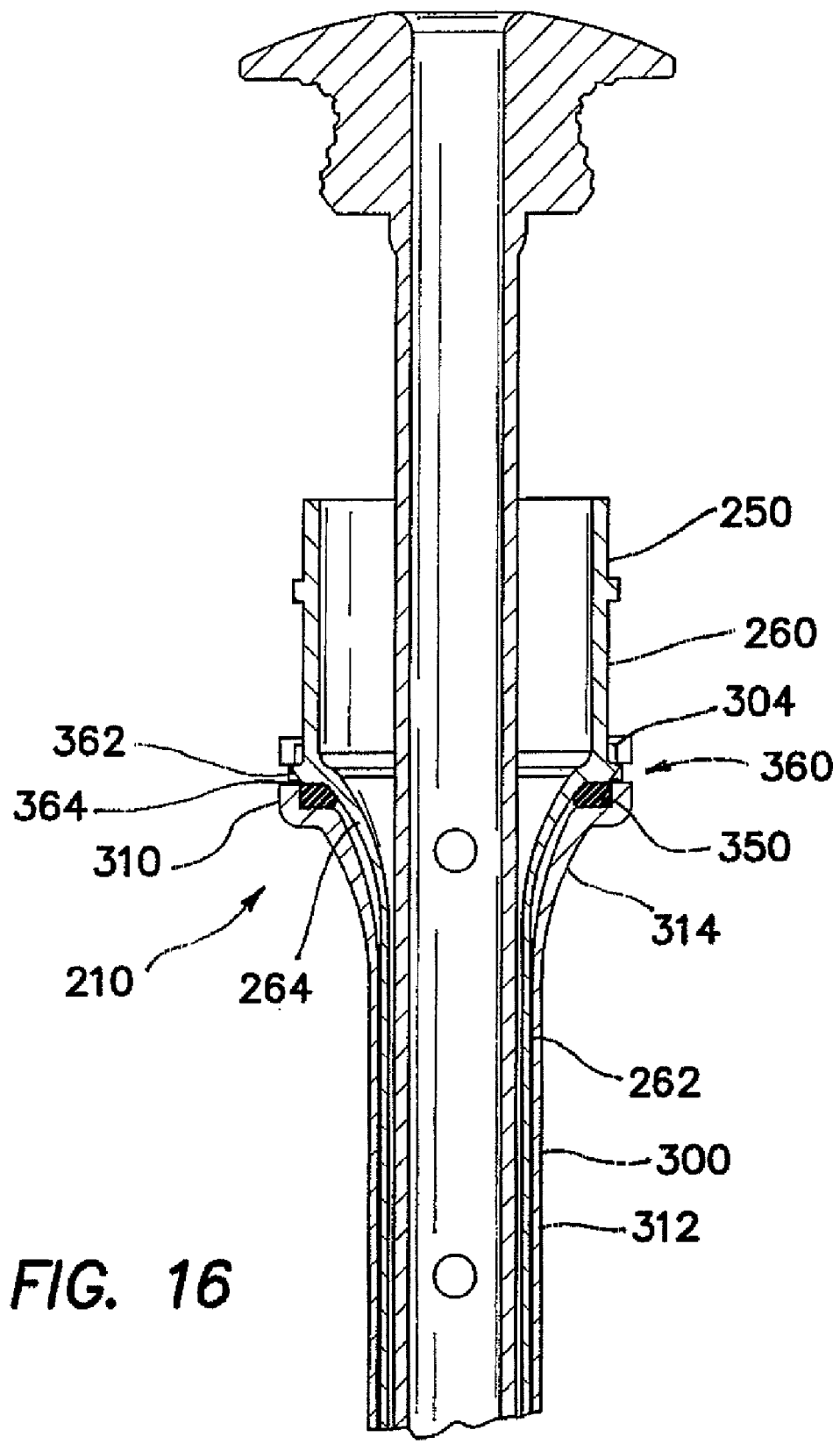
FIG. 16 is a partial plan view in cross section depicting the cannula portion, the sleeve portion, a seal, and an obturator of the balloon trocar of FIG. 13.

As stated above, the cannula assembly 210 includes the cannula 250 and the sleeve 300. Referring now to FIG. 16, to substantially prevent gas or fluid from leaking between the proximal end 304 of the sleeve 300 and the proximal portion 260 of the cannula 250, a seal, such as an o-ring 350, may be positioned between the cannula and the sleeve. In one aspect the seal, such as the o-ring 350, is positioned between the outer surface of the cannula 250 and the inner surface of the sleeve 300. In another aspect, the outer surface of the distal region of the proximal portion 260 of the cannula 250 may include a substantially flat surface, such as a planar surface or a chamfered surface, which communicates between the proximal portion 260 of the cannula and either the transition region 264 or the distal portion 262 of the cannula. Similarly, the inner surface of the distal region of the proximal portion 310 of the sleeve 300 may include a substantially flat surface, such as a planar surface or a chamfered surface, which communicates between the proximal portion 310 of the sleeve and either the transition region 314 or the distal portion 312 of the sleeve. In this aspect, the seal, such as the o-ring 350, is positioned between the flat surface on the outer surface of the distal region of the proximal portion 260 of the cannula 250 and the flat surface on the inner surface of the distal region of the proximal portion 310 of the sleeve 300.

Referring to FIGS. 13-17, the cannula 250 and the sleeve 300 are coupled together at the proximal portion 260 of the cannula and the proximal portion 310 of the sleeve at a position proximal to the seal, such as the o-ring 350. In one aspect, the means for coupling the proximal portion 260 of the cannula 250 and the proximal portion 310 of the sleeve 300 includes a snap fitting 360 having at least one projection 362 on the outer surface of the cannula and at least one notch 364 on the inner surface of the sleeve. Alternatively, the projection may be on the inner surface of the sleeve and the notch may be on the outer surface of the cannula. The at least one projection 362 and the at least one notch 364 are positioned such that when the projection is positioned within the notch, the seal, such as the o-ring 350, is compressed sufficiently to form a seal between the cannula 250 and the sleeve 300. In one aspect, the seal, such as the o-ring 350, is made from a soft, compressible material. In one aspect, the o-ring 350 is made of a silicone having a hardness of about 40 Shore A. In one aspect, the snap fitting 360 includes two projections 362 positioned substantially circumferentially opposite each other on the outer surface of the cannula and two notches 364 positioned substantially circumferentially opposite each other on the inner surface of the sleeve 300. Other means for coupling the sleeve 300 to the cannula 250 that are well known in the art may also be used, such as other mechanical means or adhesive bonding.

Figure 18:
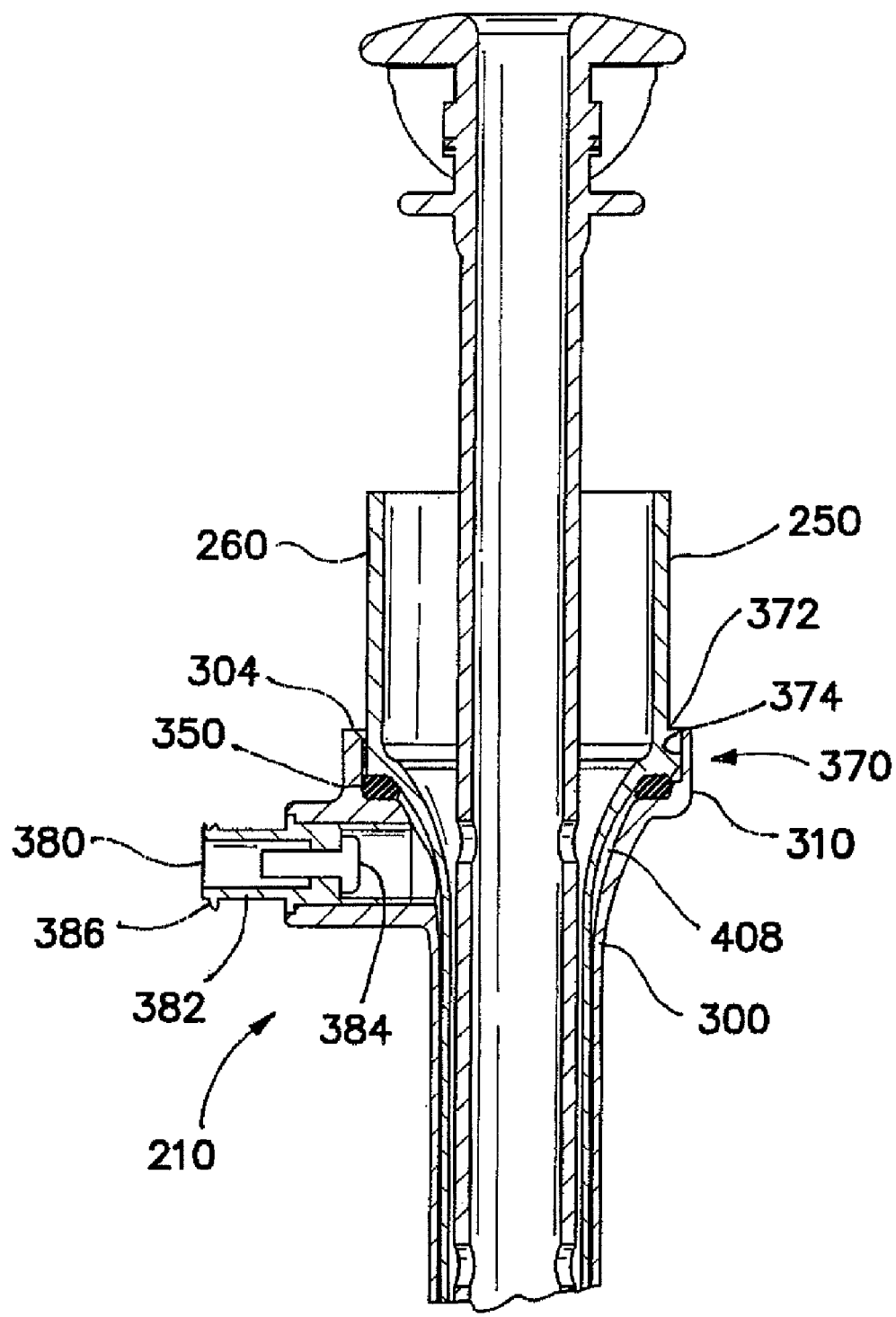
FIG. 18 is a partial plan view in cross section similar to FIG. 16 and including a port portion of the sleeve portion of the balloon trocar.

Referring to FIGS. 14, 15 and 18, the cannula assembly 210 also includes a locking means 370 to substantially prevent, or minimize, the cannula 250 and the sleeve 300 from rotating relative each other about the longitudinal axes 272, 320 while the cannula and sleeve are coupled together. In one aspect, the locking means 370 includes a projection 372 on the outer surface of the cannula 250 and a channel 374 on the inner surface of the sleeve 300. In one aspect, the projection 372 is positioned on the outer surface of the proximal portion 260 of the cannula 250 and the channel 374 is positioned on the inner surface of the proximal portion 310 of the sleeve 300 and extends to the proximal end 304 of the sleeve. Alternatively, the projection 372 may be positioned on the inner surface of the proximal portion 310 of the sleeve 300 and the channel 374 may be positioned on the outer surface of the proximal portion 260 of the cannula 250. If the channel 374 is positioned on the sleeve 300, the channel may either be through the entire thickness of the wall of the sleeve or through only a portion of the thickness of the wall of the sleeve. To substantially prevent or minimize rotation between the cannula 250 and the sleeve 300, the channel 374 is substantially longitudinal and substantially parallel to the axis 320 of the sleeve 300. The projection 372 may include any shape that fits within the walls of the channel 374 and facilitates the prevention or minimization of rotation between the cannula 250 and the sleeve 300. In one aspect, the projection 372 is substantially cylindrical while in another aspect the projection is substantially rectangular.

Figure 19:
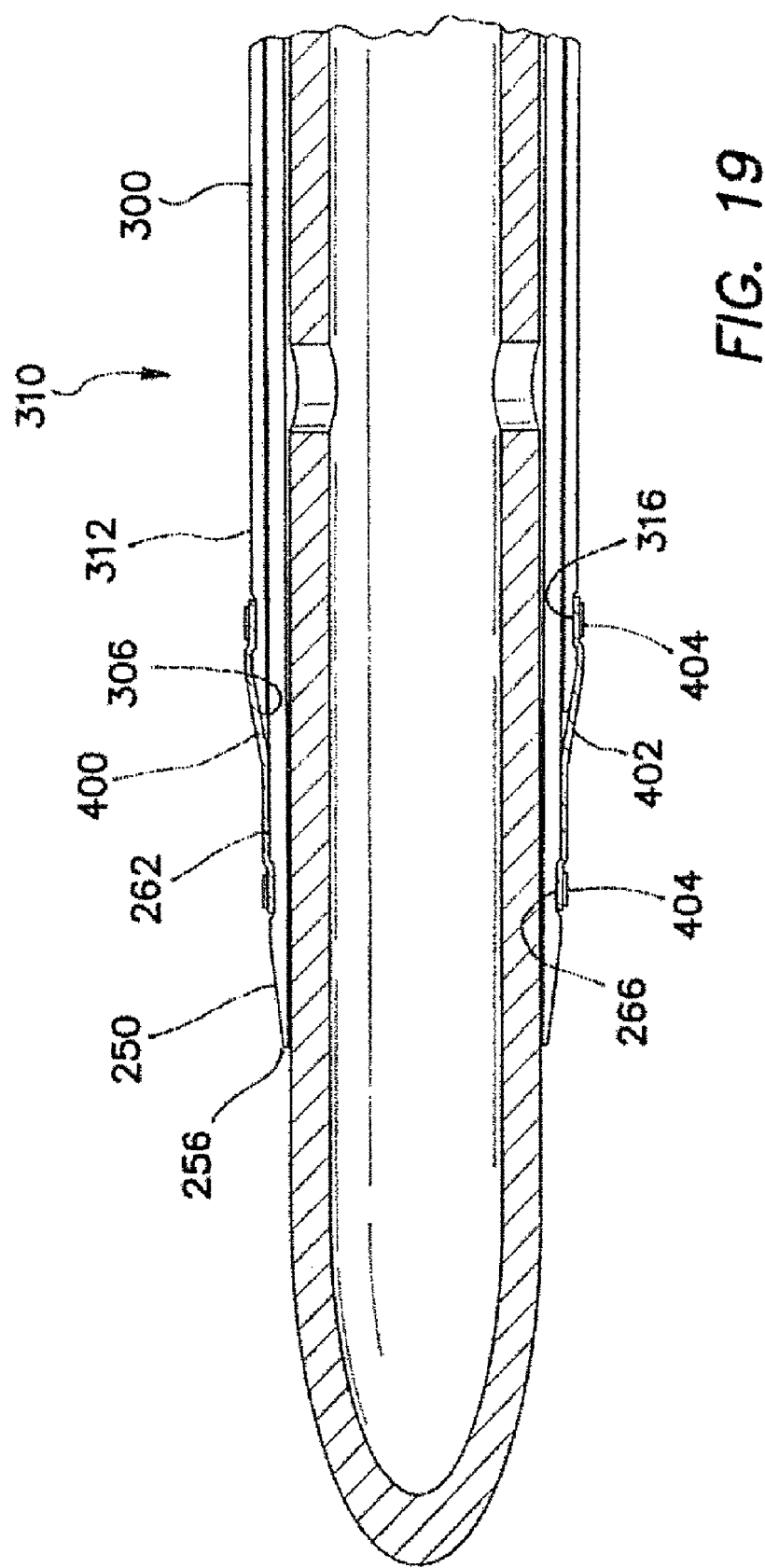
FIG. 19 is a partial plan view in cross section depicting a distal portion of the cannula portion, sleeve portion, obturator and a balloon coupled between the cannula portion and sleeve portion by windings of thread.

Referring to FIG. 19, the cannula assembly 310 also includes a balloon 400. In one aspect, the balloon includes a tubular sleeve 402. The tubular sleeve 402 may include an elastomeric material. Elastomeric materials that may be used to make the balloon 400 include silicone, polyisoprene, and urethane. In other aspects, the balloon 400 may be made of other materials, such as MYLAR, that may be folded onto the cannula 250 and sleeve 300 and inflated into a larger profile. The balloon 400 may be cut to length prior to installation onto the cannula 250 and sleeve 300 such that the balloon is sufficiently long to extend between and cover the annular grooves 266, 316 at the distal portions 262, 312 of the cannula and sleeve. The balloon 400 is slid over the distal end 256 of the cannula 250 and the distal end 306 of the sleeve 300 until it covers the annular grooves 266, 316 in the cannula and sleeve.

In one aspect, the balloon 400 is fixed in place by winding thread 404 around the balloon in the areas that overlap of the annular grooves 266, 316 at the distal portions 262, 312 of the cannula 250 and sleeve 300. Winding the balloon 400 with thread 404 forces the portion of the balloon that overlaps the annular grooves 266, 316 into the annular grooves and holds the balloon in place, thereby substantially preventing longitudinal, axial movement of the balloon along the cannula assembly. The grooves 266, 316 are of sufficient depth that forcing the balloon 400 into the annular grooves 266, 316 makes the balloon and winding 404 substantially flush to the cannula 250 and sleeve 300 at the windings, thereby making the cannula assembly 210 substantially smooth. Furthermore, forcing the balloon 400 into the annular grooves 266, 316 with the windings 404 also forms a seal between the balloon and the cannula 250 and between the balloon and the sleeve 300.

Figure 20:
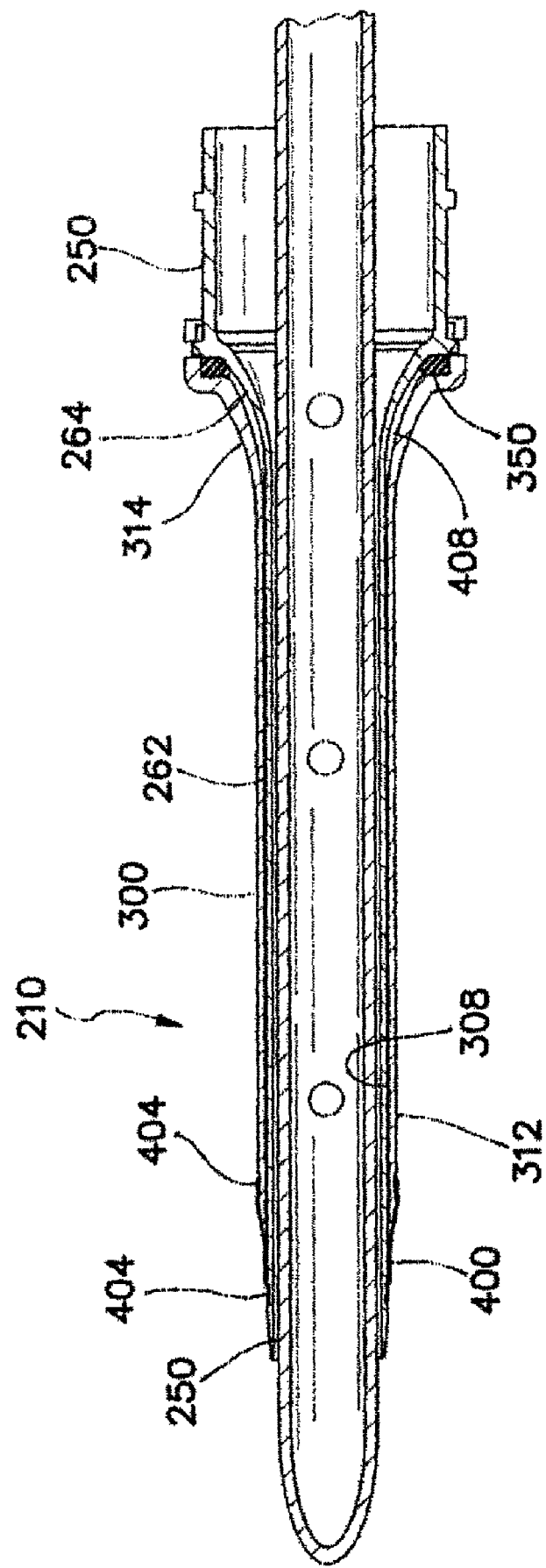
FIG. 20 is a plan view in cross section depicting the balloon trocar.

Referring to FIG. 20, the space between the outer surface of the cannula 250 with the channels 268 (see FIG. 14), the inner surface of the sleeve 300, the o-ring 350, and the balloon 400 with the windings 404 form a substantially closed chamber 408. In one aspect, the channels 268 on the outer surface of the cannula 250 are formed into the wall of the cannula so as not to increase the overall thickness of the wall of a standard cannula. The lumen 308 of the sleeve 300 may be configured to provide minimal space between the distal portion 312 of the sleeve and the distal portion 262 of the cannula 250, thereby minimizing the overall profile of the cannula assembly 210. The gap between the transition regions 264, 314 of the cannula 250 and the sleeve 300 may be larger than the gap between the distal portions 262, 312 in order to more evenly distribute gas or fluid through the channels 268 on the outer surface of the cannula 250 during inflation and deflation of the balloon.

The balloon 400 may be made to take on one of many different shapes upon inflation of the balloon. In one aspect, the balloon 400 may include a substantially toroid shape upon inflation. In another aspect, the balloon may include a disc shape upon inflation. In another aspect, the balloon 400 may be a fluted balloon. In one aspect, different shapes for the balloon 400 may be attained by varying the thickness about the tubular sleeve 402 that forms the balloon or by pre-molding a different shape for the balloon.

Figure 21:
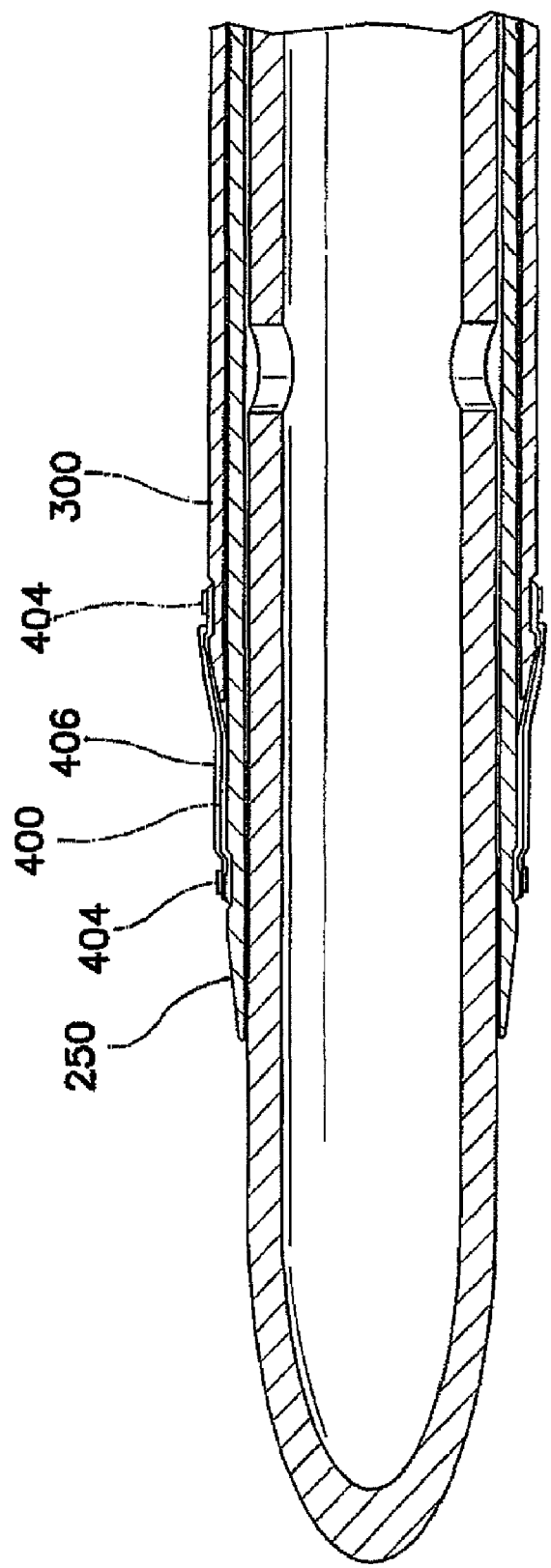
FIG. 21 is a partial plan view in cross section depicting a distal portion of the cannula portion, sleeve portion, obturator and the balloon coupled between the cannula portion and sleeve portion with a balloon having a second layer.

The balloon 400 should have sufficient impermeability properties to substantially prevent inflation gas or fluid from permeating through a wall of the balloon. Additionally, the balloon should bias toward a deflated state during deflation of the balloon. Referring to FIG. 21, an outer layer 406 may be positioned and fixed over the balloon when using a balloon material that does not possess adequate properties to bias the balloon toward deflation. The outer layer 406 may include silicone, latex, polyisoprene, rubber, or other biocompatible elastomeric materials that are well known in the art. The outer layer 406 may be wound onto the cannula 250 and sleeve 300 together with the balloon 400, as described above.

Some elastomeric materials for the balloon 400 possess inadequate impermeability properties to enable balloons made of such materials to be used without first sealing the pores in the balloon material. For example, a balloon 400 formed of silicone will have adequate properties to bias the balloon toward deflation, but it may be too porous to maintain adequate inflation for the term of a surgical procedure. In some embodiments, the inner surface of the balloon may be coated with grease to seal the pores in the balloon. In one aspect, the balloon may be formed of a porous material, such as silicone, and the grease may be silicone grease. The silicone may have adequate properties to bias the balloon toward deflation, but it may be too porous to be used independent of an additional sealing means. The silicone grease serves to seal the pores of the balloon, thereby extending the inflation time of the balloon.

To prevent or minimize the likelihood of a crease forming and creating a leak path when winding the ends of the balloon 400 with the winding 404, the periphery of the inside surface of the balloon should be about equal to, or smaller than, the periphery of the annular groove 266 on the cannula 250. In this manner, the balloon is stretched onto the cannula 250 and sleeve 300 and the ends of the balloon 400 fit snugly into the annular grooves 266, 316 of the cannula and sleeve. With the balloon being stretched in the area of the annular grooves 266, 316, it is not likely that the balloon 400 will crease when the windings 404 are applied to the balloon. However, the stretching action to place the balloon 400 onto the cannula 250 and sleeve 300 may cause uneven stretching about the perimeter of the balloon that may result in asymmetric inflation of the balloon. By applying grease to the inner surface of the balloon 400 prior to placing the balloon onto the cannula 250 and sleeve 300, the grease acts as a lubricant and permits the balloon to slide more easily over the cannula and sleeve, thereby improving assembly, and to rotate back toward a natural position about the perimeter of the balloon, thereby providing for substantially symmetric inflation of the balloon. In other words, the grease allows the balloon to substantially self-center itself, thereby substantially equalizing the stresses within the balloon material and allowing for substantially symmetric inflation of the balloon.

By applying the grease to the inner surface of the balloon 400, rather than adding an additional layer to the balloon, increases in the outer profile of the balloon are minimized. Using a silicone balloon 400 with silicone grease limits the introduction of potentially allergic materials, such as latex.

Referring again to FIG. 18, the sleeve 300 includes an inflation port 380 positioned to be distal to the seal, such as the o-ring 350. The inflation port 380 provides a pathway for gas or fluid to be introduced and removed from the chamber 408. In one aspect, the inflation port 380 may include a normally closed check valve 382 having a spring-loaded plunger 384. In a further aspect, the check valve 380 may include a Luer lock 386. It is contemplated that other inflation ports that are well known in the art may be used.

Referring again to FIG. 13, the trocar seal 220 may include a valve that provides an instrument seal in the presence of an instrument, such as the obturator 230, and a zero-seal in the absence of an instrument. The trocar seal 220 may also be removable from the cannula assembly 210. Removal of the trocar seal 220 is useful for tissue removal through the cannula assembly 210 and for rapid release of insufflation gases.

Figure 22:
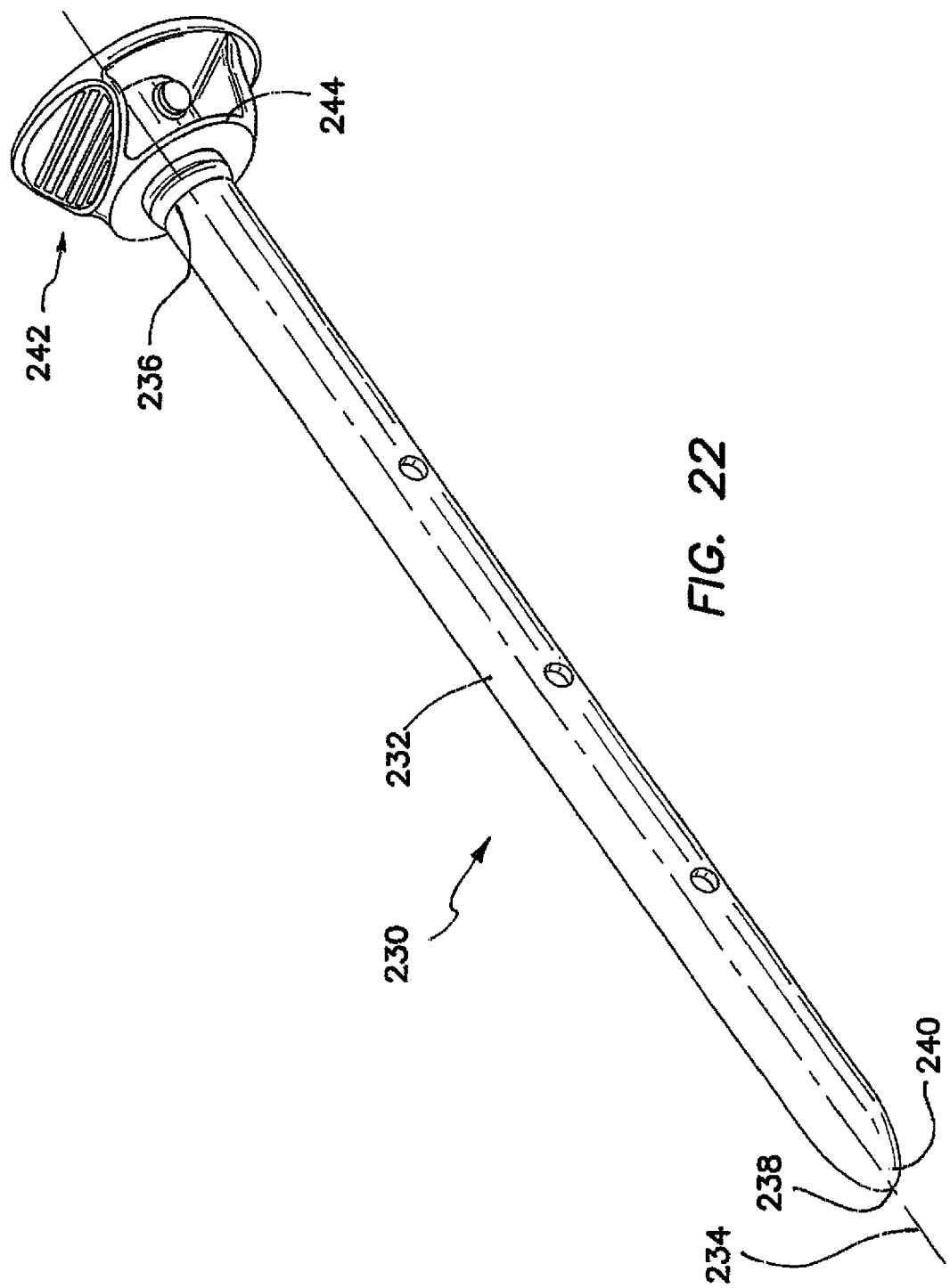
FIG. 22 is a perspective view of the obturator.

Referring to FIG. 22, the obturator 230 includes an elongate shaft 232 extending along a substantially longitudinal axis 234 between a proximal end 236 and a distal end 238. A distal tip 240 of the elongate shaft 232 may include a prolate spheroid shape. The elongate shaft 232, including the distal tip 240, is sized and configured to slide within the lumen 258 of the cannula 250 (see FIGS. 16 and 19). A proximal portion 242 of the obturator 230 may include a handle portion 244 having a larger periphery than the elongate shaft 232 to facilitate advancing and retracting the obturator within the lumen 258 of the cannula 250. In an operative position, the distal tip 240 of the obturator 230 is positioned distal to the distal end 256 of the cannula 250 and the handle portion 244 of the obturator is positioned proximal to the proximal end 254 of the cannula.

The obturator 230 may be made of a polymeric material, such as a polycarbonate. Those familiar with the art will recognize that the obturator 230 may be made of other materials that are well known in the art and are considered within the scope of the present invention. In comparison to obturators having distal tips with a spheroid shape, the distal tip 240 of the obturator 230 having a prolate spheroid shape requires a lower insertion force to insert the trocar into a body through an incision within a body wall. The prolate spheroid shape of the distal tip 240 of the obturator 230 also reduces the likelihood of injuring tissue or organs within the body cavity, in comparison to obturators having distal tips with a more pointed shape. Using the obturator 230 having a distal tip 240 with a prolate spheroid shape, the surgeon can merely nick the peritoneum and dilate or stretch the incision open with the distal tip of the obturator.

Referring again to FIG. 13, a bolster 410 may be used in conjunction with the balloon trocar 200 to assist the balloon to seal around an incision in the body wall 50 through which the balloon trocar is to be inserted with the balloon sealing the incision from within the body cavity 52. The bolster 410 is configured to perform as a cannula fixation device on the outside of the body while the balloon 400 acts as a cannula fixation device on the inside of the body. The bolster 410 is slidably adjustable along the length of the cannula assembly 210 proximal to the balloon 400 and includes a clamping device for locking the bolster in position along the length of the cannula assembly. The balloon 400, on the other hand, is fixed at a location along the length of the cannula assembly 210 and seals against the inner surface of the abdominal wall.

To facilitate the clamping features of the bolster 410, the bolster includes a base 420 and a clamping mechanism 415. The clamping mechanism 415 includes an adjustable collar 460 and a lever 500. The bolster also includes a pad 530 including a substantially incompressible gel material. The clamping features utilize an over-center lock design to maintain the bolster 410 in a fixed position along the length of the cannula assembly 210.

Figure 23:
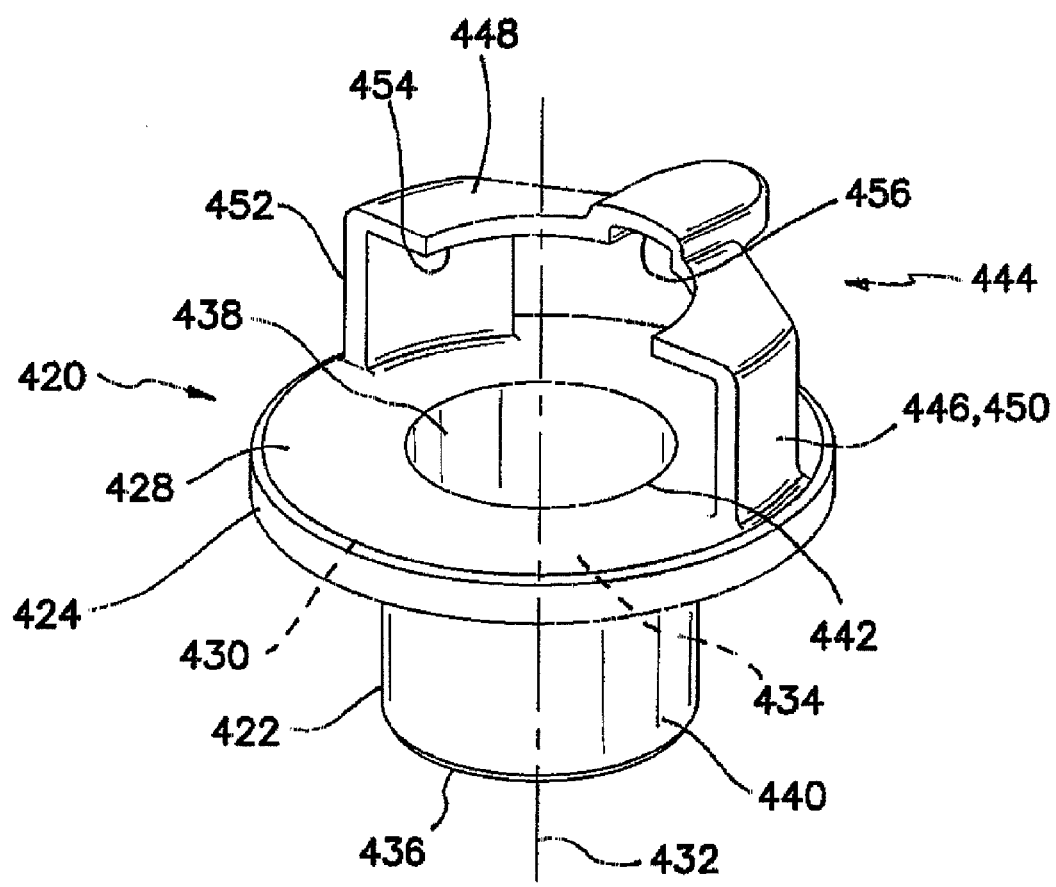
FIG. 23 is a perspective view of a base portion of the bolster of FIG. 13.

Referring to FIG. 23, the base 420 includes a sleeve 422 projecting distally from a flange 424. The flange 424 includes a proximal surface 428 and a distal surface 430. The proximal surface 428 and the distal surface 430 of the flange 424 are substantially parallel to each other and substantially perpendicular to an axis 432 of the base 420. Although the flange 424 is shown as being flat, other shapes, such as rounded shapes, may be used and are contemplated as within the scope of the invention. The sleeve 422 portion of the base 420 includes a proximal end 434, a distal end 436, and a lumen 438 therebetween. The lumen 438 is sized to receive and slidably engage the sleeve 300 of the cannula assembly 210. An outer surface 440 of the sleeve 422 portion of the base 420 may include a substantially cylindrical shape. The lumen 438 of the sleeve 422 portion of the base 420 extends through the flange 424, thereby forming an aperture 442 in the flange.

A clamp receptacle 444 extends proximally from the proximal surface 428 of the flange 424. The clamp receptacle 444 includes at least one riser 446 extending from the proximal surface 428 of the flange 424 and a platform 448 extending from the at least one riser 446. In one aspect, the clamp receptacle 444 includes a first riser 450 and a second riser 452 with the platform 448 extending between the first and second risers. The platform 448 is shaped so as to not extend over the aperture 442 in the flange 424. In other words, the platform 448 provides clearance for the cannula assembly 210 such that the bolster 410 may slidably engage the cannula assembly without the platform interfering with the engagement. The platform 448 includes a distal surface 454 that is substantially parallel to the proximal surface 428 of the flange 424. As will be described below, the distance between the distal surface 454 of the platform 448 and the proximal surface 428 of the flange 424 is sufficient to receive the clamp mechanism 415 portion of the bolster 410. The distal surface 454 of the platform includes a substantially linear slot 456 extending radially therethrough. In one aspect, the base may be made of a polymeric material, such as a polycarbonate. However, it is contemplated that other materials, such as metals and composites, may be used.

Figure 24:
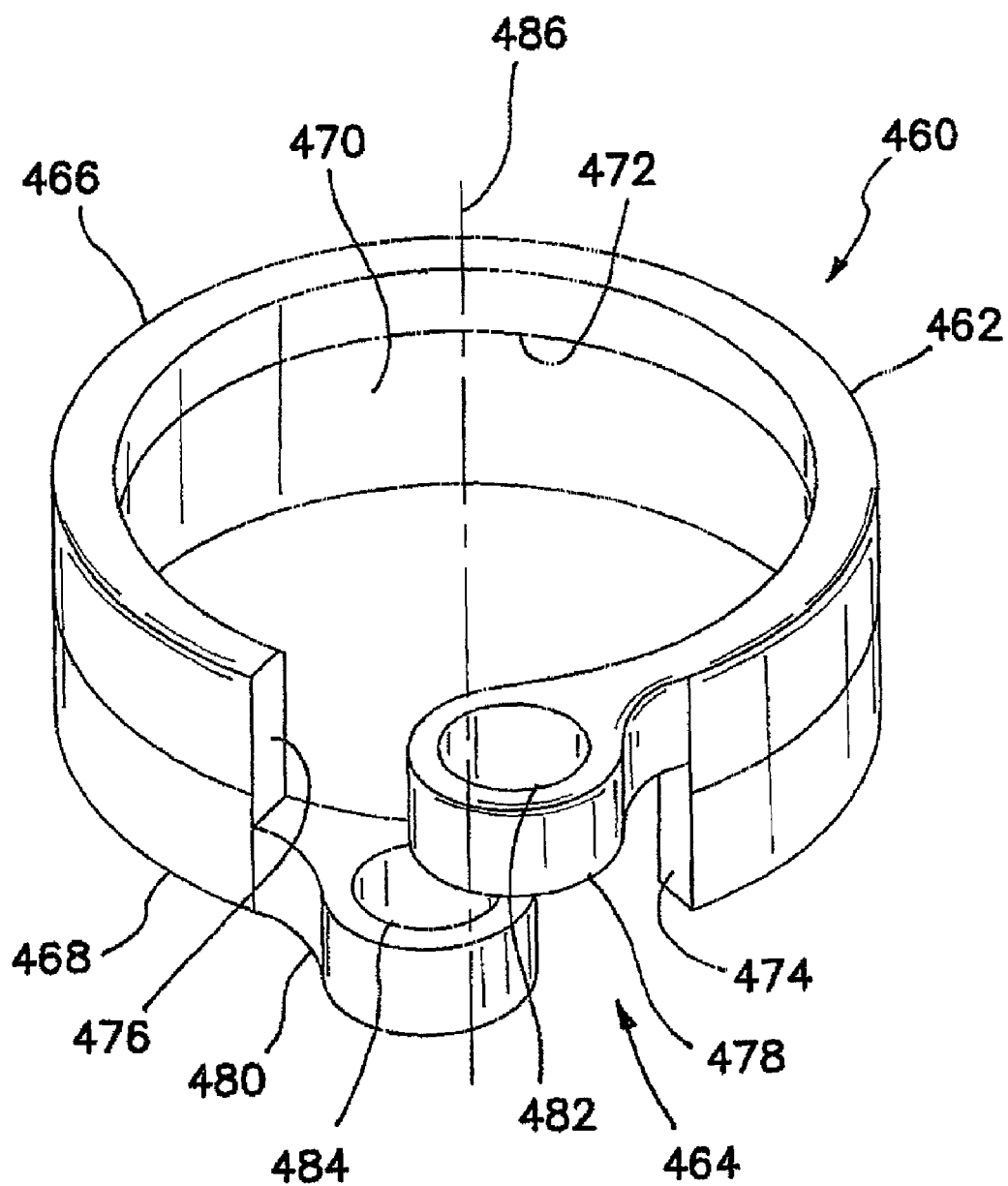
FIG. 24 is a perspective view of a collar portion of the bolster of FIG. 13.

Referring to FIG. 24, the collar 460 portion of the clamping mechanism 415 of the bolster 410 includes a substantially circumferential ring 462 defining a split 464. The collar 460 further includes a proximal end 466, a distal end 468, and an inner surface 470. The inner surface 470 of the collar 460 may include a counterbore configuration forming a ledge 472 therein. The split 464 in the collar 460 forms a first end 474 of the collar 460 and a second end 476 of the collar. The collar 460 is flexible in order to adjust the fit of the collar over the cannula assembly 210. More particularly, the first end 474 and the second end 476 of the collar may be brought closer together to create sufficient friction between the bolster 410 and the cannula assembly 210 to substantially fix the bolster in place along the length of the cannula assembly. The first end 474 and the second end 476 of the collar may also be spread apart to reduce or substantially eliminate the friction between the bolster 410 and the cannula assembly 210 so that the bolster may slide along the length of the cannula assembly.

To facilitate control of the distance between the first end 474 and the second end 476 of the collar 460, a first tab 478 extends from the first end 474 of the collar and a second tab 480 extends from the second end 476 of the collar. In one aspect, the first and second tabs 478, 480 may extend circumferentially from the first and second ends 474, 476, respectfully. In other aspects, the first and second tabs 478, 480 may extend tangentially or radially from the first and second ends 474, 476, respectfully, or in any other manner that is well known in the art. The first tab 478 includes a first aperture 482 extending longitudinally therethrough and the second tab 480 includes a second aperture 484 extending longitudinally therethrough. The first and second apertures 482, 484 extend substantially parallel to an axis 486 of the collar 460. As will be discussed below, the lever 500 interacts with the tabs 478, 480 to control the distance between the first and second ends 474, 476 of the collar 460. The collar may be made of a polymeric material, such as polycarbonate. However, it is contemplated that other materials, such as metals and composites, may be used.

Figure 25:
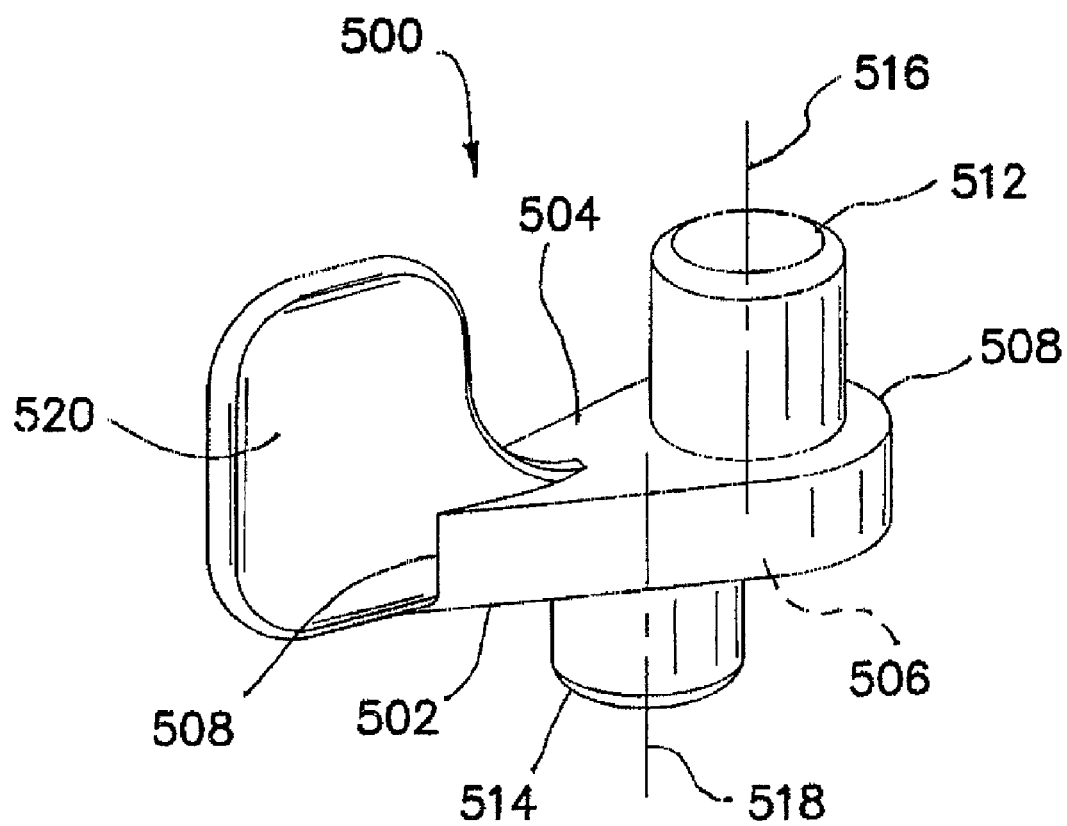
FIG. 25 is a perspective view of a lever portion of the bolster of FIG. 13.

Referring to FIG. 25, the lever 500 includes an arm 502 having a first, proximal surface 504, a second, distal surface 506, a first end 508 and a second end 510. The proximal and distal surfaces 504, 506 of the arm 502 are substantially parallel to each other. A substantially cylindrical first pin 512 extends proximally from the proximal surface 504 of the arm 502 proximate the first end 508 and a substantially cylindrical second pin 514 extends distally from the distal surface 506 proximate the first end. The first and second pins 512, 514 each extend substantially perpendicular from the proximal and distal surfaces 504, 506, respectively, of the arm 502. An axis 516 of the first pin 512 and an axis 518 of the second pin 514 are substantially parallel to each other, but are also offset from each other. In one aspect, the first pin 512 is closer to the first end 508 of the arm 502 than is the second pin 514. The peripheries of the first and second pins 512, 514 are sized to fit within the first and second apertures 482, 484, respectively, of the tabs 478, 480 of the collar 460. In one aspect, there may be a tab 520 positioned at the second end of the arm 502 to facilitate rotation of the lever 500 when it is assembled into the bolster 410.

Figure 26:
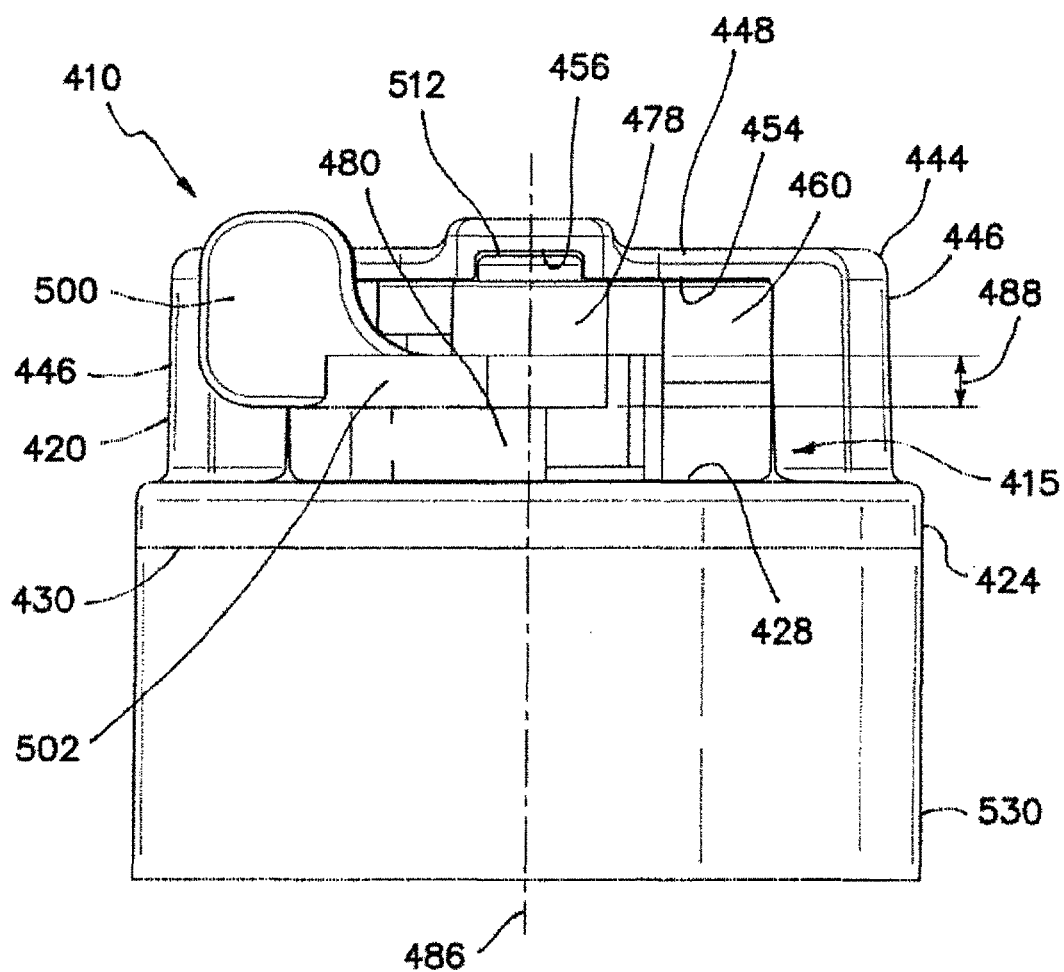
FIG. 26 is a side view of the bolster of FIG. 13.

Referring to FIG. 26, there is a space 488 between a distal surface of the first tab 478 of the collar 460 and a proximal surface of the second tab 480 of the collar. In one aspect, the distal surface of the first tab 478 and the proximal surface of the second tab 480 are substantially flat, substantially parallel to each other and substantially perpendicular to the axis 486 of the collar 460. The space 488 is sized to receive the arm 502 of the lever 500. The lever 500 is coupled to the collar 460 by manipulating the arm 502 of the collar into the space 488 between the first and second tabs 478, 480 of the collar and inserting the first pin 512 of the lever into the first aperture 482 (see FIG. 24) in the first tab 478 of the collar 460 and inserting the second pin 514 (see FIG. 25) of the lever into the second aperture 484 (see FIG. 24) in the second tab 480 of the collar. In this manner, the lever 500 is pivotally coupled to the collar 460. In one aspect, the first pin 512 of the lever is sufficiently long to extend beyond the proximal surface of the first tab 478 of the collar 460, while the second pin 514 is substantially flush or below flush with the distal surface of the second tab 480 of the collar.

Figure 27:
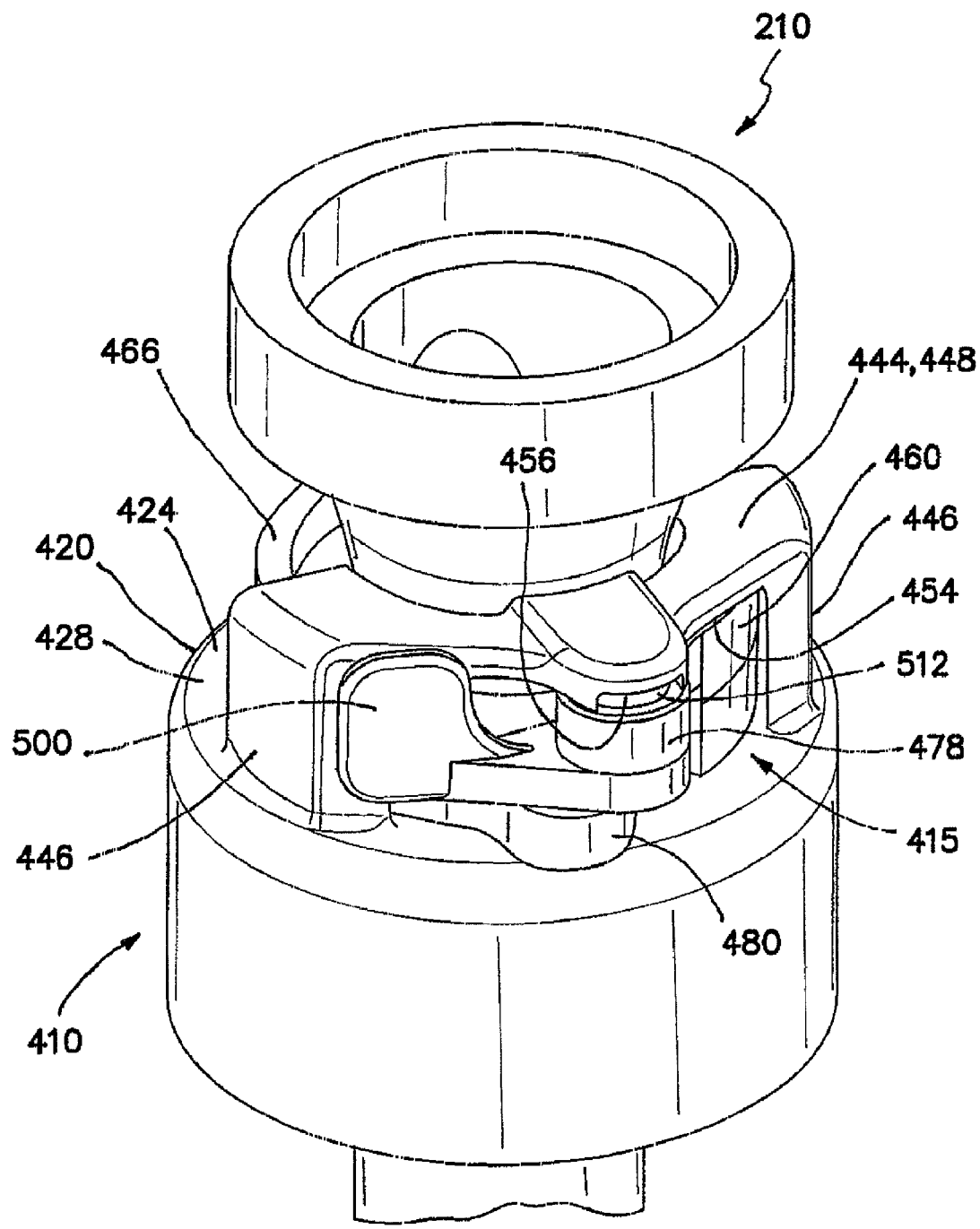
FIG. 27 is a perspective view of the bolster coupled to the sleeve portion of the balloon trocar.

With reference to FIG. 27 and continued reference to FIG. 26, to couple the clamping mechanism 415, including the collar 460 and lever 500, to the base 420, the collar and lever are inserted into the clamp receptacle 444 portion of the base. More particularly, the clamping mechanism 415 is inserted between the proximal surface 428 of the flange 424 portion of the base 420 and the distal surface 454 of the platform 448 of the clamp receptacle 444 portion of the base such that the collar 460 is nested between the flange 424, the platform 448, and the at least one riser 446 portion of the clamp receptacle 444. Further, the first and second tabs 478, 480 of the collar 460 and the first and second pins 512, 514 (see FIGS. 24 and 25) of the lever 500 are positioned between the proximal surface 428 of the flange 424 portion of the base 420 and the distal surface 454 of the platform 448. The distance between the proximal surface 428 of the flange 424 portion of the base 420 and the distal surface 454 of the platform 448 is sufficient for the clamp mechanism 415 to slidably engage within the clamp receptacle 444, yet also sufficiently low to maintain the lever 500 and collar 460 of the clamp mechanism 415 in an engaged relationship with each other during activation of the lever to maintain the clamping force of the collar against the cannula assembly 210. In one aspect, the first pin 512 of the lever 500, which extends proximally beyond the proximal surface of the first tab 478, is positioned within the slot 456 on the distal surface 454 of the platform 448 to facilitate maintaining the position of the first and second tabs 478, 480 of the collar 460 and the first and second pins 512, 514 of the lever 500 between the proximal surface 428 of the flange 424 portion of the base 420 and the distal surface 454 of the platform 448.

Referring to FIGS. 13 and 27, the bolster 410 is slidably mounted onto the cannula assembly 210 by inserting the distal end 256 of the cannula distally through the proximal end 466 of the collar 460, through the aperture 442 (see FIG. 23) of the flange 424 of the base 420, and through the sleeve 422 (see FIG. 23) of the base. The bolster 410 and cannula assembly 210 are slid relative to each other until the distal end 436 of the sleeve 422 (see FIG. 23) of the base 420 is proximal to the balloon 400 (see FIG. 19).

Figure 28:
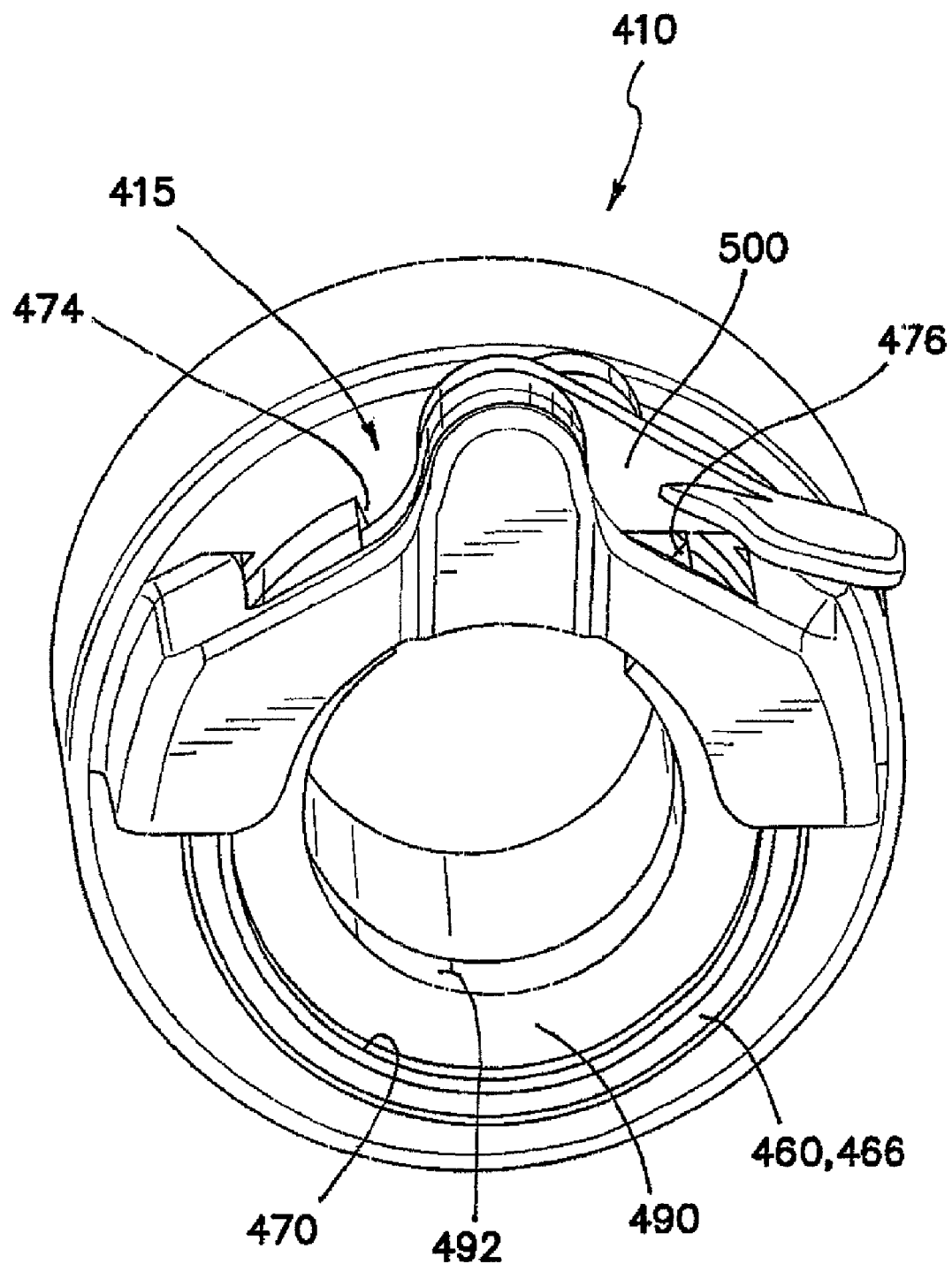
FIG. 28 is an end perspective view of the bolster of FIG. 13.

Referring to FIG. 28, when viewing the proximal end 466 of the collar 460 and lever 500 (looking distally), the distance between the first and second ends 474, 476 of the collar is at its maximum when the lever is in a first, clockwise position. Rotating the lever 500 in a counter clockwise direction moves the first and second ends 474, 476 of the collar 460 closer together, reducing the circumference of the collar and tightening the collar against the cannula assembly 210 (see FIG. 13). The change in circumference of the collar 460 as the lever 500 is rotated is caused by the offset between the first pin 512 and the second pin 514 of the lever (see FIG. 25). The circumference of the collar 460 is at its smallest when the lever is rotated about 180° from the first position. To facilitate the over-center lock design features of the clamping mechanism 415, the lever 500 is rotated from the first position more than about 180° to a second position. In this manner, as the lever 500 is rotating from the first position, the circumference of the collar 460 reduces until the lever has rotated about 180°, then expands slightly until the lever is positioned at the second position. With the lever 500 in the second position, higher pressure is initially required to rotate the lever away from the second position in a clockwise direction to the first position because the circumference of the collar 460 is reduced until the lever reaches the position that is about 180° from the first position. The higher pressure that is required protects against inadvertent release of the clamp mechanism 415. Although the clamp mechanism 415 was described in detail, those familiar in the art will recognize that other clamp mechanisms that are well known in the art may be used with satisfactory results. In one aspect, the inner surface 470 of the collar clamps directly against an outer surface 322 of the sleeve 300 portion of the cannula assembly 210. In another aspect, the bolster 410 includes a compressible ring 490 positioned inside the collar 460. The ring 490 may be seated against the ledge 472 on the inner surface 470 of the collar 460. The inner surface 492 of the ring 490 is sized to permit the bolster 410 to slide along the cannula assembly 210 when the lever 500 is in the first position and to be compressed against the outer surface 322 of the sleeve 300 portion of the cannula assembly when the lever is in the second position. In this manner, the compressed ring 490 ensures that there is sufficient friction between the bolster 410 and the cannula assembly 210 when the lever is in the second position to maintain the position of the bolster along the cannula assembly. In one aspect, the ring 490 is made of an incompressible elastomeric material, such as silicone. In one aspect, the ring 490 is molded from a soft elastomeric material, such as a silicone having a hardness of about 40 Shore A durometer. Those familiar in the art will recognize that other materials that are well known in the art may be used and are contemplated to be within the scope of the invention.

With the bolster 410 mounted onto the cannula assembly, the ring 490 makes the collar 460 substantially self-centering around the cannula assembly 210. Having the first pin 512 of the lever 500 extending into the slot 456 on the distal surface 454 of the platform 448 substantially prevents the clamping mechanism 415 from rotating about the base 420 when the bolster is positioned on the cannula assembly 210 and the lever 500 is in the second position. This in turn substantially prevents the bolster 410 from rotating about the cannula assembly 210.

Referring again to FIGS. 13 and 26, to facilitate assistance of sealing the balloon 400 around the incision in the body wall, the bolster 410 includes a substantially annular gel pad 530 coupled to the distal surface 430 of the flange 424 portion of the base 420 and around the outer surface 440 of the sleeve 422 (see FIG. 23) portion of the base. In one aspect, the gel 530 is substantially incompressible. Since the gel pad 530 is substantially incompressible, it does not need to be as thick as the foam pads 180 of the prior art. Having a thinner pad provides the cannula assembly 210 with more usable length. The gel pad 530 may operate as a backup seal for the incision to help protect against leaks that might develop between the balloon and the inner surface of the body wall. In one aspect, the gel pad 530 may be between about 3.0-20.0 mm thick. However, in another aspect the gel pad 530 may be thicker to promote the sealing features of the gel pad.

The gel pad 530 is made of a gel and may be attached to, formed or integrated with the base 420. In one aspect, the gel is an elastomeric gel. In one aspect, the gel can be prepared by mixing a triblock copolymer with a solvent for the midblocks. The endblocks are typically thermoplastic materials such as styrene and the midblocks are thermoset elastomers such as isoprene or butadiene, e.g., Styrene-Ethylene-Butylene-Styrene (SEBS). In one aspect, the solvent used is mineral oil. Upon heating this mixture or slurry, the midblocks are dissolved into the mineral oil and a network of the insoluble endblocks forms. The resulting network has enhanced elastomeric properties over the parent copolymer. In one aspect, the triblock copolymer used is KRATON G1651. Once formed, the gel is substantially permanent and by the nature of the endblocks processable as thermoplastic elastomers henceforward. The mixture or slurry has a minimum temperature at which it becomes a gel, i.e., the minimum gelling temperature (MGT). This temperature in one aspect corresponds to the glass transition temperature of the thermoplastic endblock plus a few degrees. For example, the MGT for the mixture of KRATON G1651 and mineral oil is about 120° C. When the slurry reaches the MGT and the transformation to a gel state takes place, the gel becomes more transparent, thereby providing a means for visually confirming when the transformation of the slurry to the gel state is substantially complete and that the gel may be cooled. In addition to triblocks, there are also diblock versions of the materials that may be used where Styrene is present at only one end of the formula, for example, Styrene-Ethylene/Butylene (SEB).

For a given mass of slurry to form into a complete gel, the entire mass of the slurry is heated to the MGT and remains heated at the MGT for sufficient time for the end blocks to form a matrix of interconnections. The slurry will continue to form into gel at temperatures above the MGT until the slurry/gel reaches temperatures at which the components within the slurry/gel begin to decompose or oxidize. For example, when the slurry/gel is heated at temperatures above 250° C., the mineral oil in the slurry/gel will begin to be volatile and oxidize. Oxidizing may cause the gel to turn brown and become oily.

The speed at which a given volume of slurry forms a gel is dependant on the speed with which the entire mass of slurry reaches the MGT. Also, with the application of temperatures higher than the MGT, this speed is further enhanced as the end block networks will distribute and form more rapidly.

The various base formulas may also be alloyed with one another to achieve a variety of intermediate properties. For example, KRATON G1701X is a 70% SEB 30% SEBS mixture with an overall Styrene to rubber ratio of 28/72. It can be appreciated that an almost infinite number of combinations, alloys, and Styrene to rubber ratios can be formulated, each capable of providing a low durometer, high elongation, and good tear strength.

It is contemplated that the gel material may also include silicone, soft urethanes and even harder plastics with the addition of a foaming agent that provide the desired qualities for the bolster to assist the balloon 400 to seal against the inner surface of the body wall 52. The silicone material may be of the types currently used for electronic encapsulation. The harder plastics may include PVC, Isoprene KRATON neat, and other KRATON/oil mixtures. In the KRATON/oil mixture, oils such as vegetable oils, petroleum oils and silicone oils may be substituted for the mineral oil. Any of the gel materials contemplated could be modified to achieve different properties such as enhanced lubricity, appearance, and wound protection. Additives may be incorporated directly into the gel or applied as a surface treatment. Other compounds may be added to the gel to modify its physical properties or to assist in subsequent modification of the surface by providing boding sites or a surface charge. Additionally, oil based colorants may be added to the slurry to create gels of different colors.

In one aspect, the mixture/slurry used with the various aspects of the bases 420 that are described herein are composed of 90% by weight of mineral oil and 10% by weight of KRATON G1651. From a thermodynamic standpoint, this mixture behaves similar to mineral oil. Mineral oil has a considerable heat capacity and therefore at about 130° C. it can take 3 or 4 hours to heat a pound of the slurry sufficiently to form a homogeneous gel. Once formed, the gel can be cooled as quickly as practical with no apparent deleterious effects on the gel. This cooling, in one aspect, is accomplished with cold-water immersion. In another aspect the gel may be air-cooled. Those familiar with the art will recognize that other cooling techniques that are well know in the art may be employed and are contemplated as within the scope of the present invention.

Many of the properties of the KRATON/oil mixture will vary with adjustments in the weight ratio of the components. In general, the greater the percentage of mineral oil, the less firm the mixture; the greater the percentage of KRATON, the more firm the mixture.

If the slurry is permitted to sit for a prolonged period of time, the copolymer, such as KRATON, and the solvent, such as mineral oil, may separate. The slurry may be mixed, such as with high shear blades, to make the slurry more homogeneous. However, mixing the slurry may introduce or add air to the slurry. To remove air from the slurry, the slurry may be degassed. In one aspect, the slurry may be degassed in a vacuum, such as within a vacuum chamber. In one aspect, the applied vacuum may be 0.79 meters (29.9 inches) of mercury, or about 1.0 atmosphere. The slurry may be stirred while the slurry is under vacuum to facilitate removal of the air. During degassing within a vacuum, the slurry typically expands, then bubbles, and then reduces in volume. The vacuum may be discontinued when the bubbling substantially ceases. Degassing the slurry in a vacuum chamber reduces the volume of the slurry by about 10%. Degassing the slurry helps reduce the potential of the finished gel to oxidize.

Degassing the slurry tends to make the resultant gel firmer. A degassed slurry composed of about 91.6% by weight of mineral oil and 8.4% by weight of KRATON G1651, an eleven-to-one ratio, results in a gel having about the same firmness as a gel made from a slurry that is not degassed composed of 90% by weight of mineral oil and 10% by weight of KRATON G1651, a nine-to-one ratio.

The gel in various aspects may be gamma sterilized. As such, the relative or comparative simplicity of qualifying the sterilization process, for example of gamma versus ethylene oxide, of the gel and the device with the gel is desirable. However, under gamma sterilization large bubbles can form in the gel causing potential cosmetic or aesthetic issues in the sterilized devices. The bubbles are more than 99% room air and as such removal of the dissolved air in the slurry prior to forming the slurry into gel is performed. For example, the slurry may be degassed via vacuum as described above and turned into gel by heat. Bubbles may still form in the gel during gamma sterilization but disappear in a period of about 24 to 72 hours. In one aspect, the percentage of dissolved gas in the mineral oil at room temperature is about 10%. The removal of the air in the gel has an additional effect of making the gel firmer. This however is counterbalanced by the softening effect of gamma radiation on the gel during gamma sterilization.

In one aspect, if the gel is to be gamma sterilized, the gel may include about 90% mineral oil by weight and about 10% KRATON by weight. As stated above, degassing the slurry has the effect of making the gel firmer, however, the gamma radiation softens the gel to substantially the same firmness as a gel having about 90% mineral oil by weight and about 10% KRATON by weight that is not degassed or gamma sterilized.

In one aspect, cyanoacrylate, e.g., SUPERGLUE or KRAZY GLUE, may be used to bond or otherwise attach the gel pad 530 to the base 420. The glue may attach to either the rubber or styrene component of the tri-block and the bond is frequently stronger than the gel material itself.

In another aspect, a solvent is used to dissolve the plastics in the base 420 and the polystyrene in the gel. The solution of solvent is applied to the gel and base 420 in either a spray or dip form. In effect the solution melts both the plastic of the base as well as the polystyrene in the gel to allow a chemical bond to form between the two, which remains when the solvent evaporates.

Polyethylene can be dissolved in mineral oil and then applied to the gel. The mineral oil will not evaporate but will over time absorb into the gel and impart a polyethylene layer on the gel that may have beneficial properties.

In one aspect, the gel is cast into a mold containing the base 420. Adhesion between the gel pad 530 and the base 420 can be achieved by using KRATON polymer or a similar material in the base. The polystyrene in the gel is identified as achieving adhesion with polyphenylene oxide (PPO), polystyrene and others.

In the casting process, the gel pad 530 and the base 420 are heated to a temperature above about 130° C. and held at that temperature for several hours, e.g., about 3 to 4 hours. The temperature used is not sufficient to deform the base 420.

In one aspect, the base 420 comprises a polymer, e.g., polyethylene (PE). In one aspect, the polyethylene is a low-density polyethylene (LDPE) or high-density polyethylene (HDPE), or ultra high molecular weight polyethylene (UHMWPE). In one aspect, the base 420 may be made of a polymer, such as polycarbonate and may be fabricated by methods including injection molding. The gel includes mineral oil. PE has a higher molecular weight than mineral oil. PE is dissolved by mineral oil at high temperatures. As such, as the PE and mineral oil in the gel intermix as both are heated to and held at temperatures above about 130° C., a bond between the PE and gel is formed.

In one aspect, the base 420 is made of polycarbonate. The polycarbonate of the base does not form bonds with gel at 130° C. However during casting, by raising the temperature to about 150° C. for a few minutes, bonding occurs between the gel pad 530 and the base. As such, heating the gel and base to temperatures at which both the polystyrene of the gel and the polycarbonate are simultaneously beyond their melt points allows bonds to form between the gel pad 530 and the base 420. Alternatively, the gel and base may be heated to near or at the glass transition temperature of the polycarbonate base 420 to form the bond between the gel pad 530 and the base.

In one aspect, casting the gel pad 530 with the base 420 to form the bolster 410 includes placing the base into a casting mold. The mold may be made of aluminum, copper, brass, or other mold material having good heat dissipation properties. However, those familiar with the art will recognize that other mold materials having lower heat dissipation properties will produce acceptable parts and these are contemplated as within the scope of the present invention.

The mold having the base 420 is filled with the slurry. To facilitate filling voids in the mold with the slurry, the slurry may be preheated, for example, to about 52° C. (125° F.). Preheating the slurry to a temperature below the MGT reduces the viscosity of the slurry and allows the slurry to flow more easily. As stated above, the slurry may have been degassed in a vacuum. The slurry may be degassed again within the mold after the mold is filled to remove air that may have been introduced during the filling of the mold and to facilitate flow of the slurry into voids in the mold. Heat is applied to the mold having the base 420 and the slurry, such as in an oven, until the slurry attains a temperature of about 150° C. As stated above, the slurry turns into gel at about 120° C., however, at about 150° C., the gel can bond to a polycarbonate base 420. Depending on the material used to fabricate the base 420, bonding may take place at temperatures other than about 150° C. If the base 420 is fabricated of a material having a lower melting point than 120° C., then the gel pad 530 may be molded separately and then bonded to the base 420.

Once the temperature of the gel reaches about 150° C., the bolster 410 may be cooled, such as by air-cooling, cold-water immersion, or other cooling means that are well known in the art. At 150° C. the gel is soft and if it were distorted during cooling it would set with the distortion included. To reduce the likelihood of distorting the gel pad 530, the bolster 410 may be cooled within the mold. Cooling times may vary based on parameters including size and configuration of the mold, quantity of gel, temperature and quantity of cooling medium, cooling medium properties and the mold material. Whether cooling with air or water, the final properties of the gel are substantially the same. The bolster 410 is typically cooled to about ambient room temperature, but may be cooled to lower temperatures. The bolster 410 may be removed from the mold at any time after the gel has set.

When removed from the mold, the gel typically has a tacky surface. The gel pad 530 may be coated with a powder, such as cornstarch, to substantially reduce or eliminate the tackiness of the cured gel.

As stated above, in another aspect, the gel pad 530 may be molded separately from the base 420 and subsequently bonded to the base. In one aspect, the gel pad 530 may be molded into a slug. Since the gel 530 is being molded separate from the base 420, the slurry only needs to be heated until it reaches about 120° C. and completes the transformation from slurry into gel and the gel becomes substantially transparent. The gel pad 530 may then be placed onto the base 420. The gel pad 530 and base 420 are heated to a sufficient temperature for the polystyrene of the gel and the polymer of the base 420 to form bonds between the gel pad 530 and the base. Molding the gel pad 530 separately from the base 420 and heat bonding the gel pad to the base at a later time is especially useful when the base is made of a material that has a lower melting temperature than the MGT. In such situations, the gel pad 530 can be molded first and heat bonded to the base 420 without melting the base.

During a surgical procedure in which the balloon trocar 200 may be used, a surgeon may gain access to the abdominal cavity 52 through the abdominal wall 50 by using the "Hassan" or "cut-down" technique. However, use of the Hassan or cut-down technique often leaves a defect larger than the trocar that will be located through the incision. Therefore, it is necessary to provide a means to seal the incision after the trocar has been inserted in order to insufflate the patient's abdominal cavity. The balloon trocar 200 provides such a seal.

Figure 17:
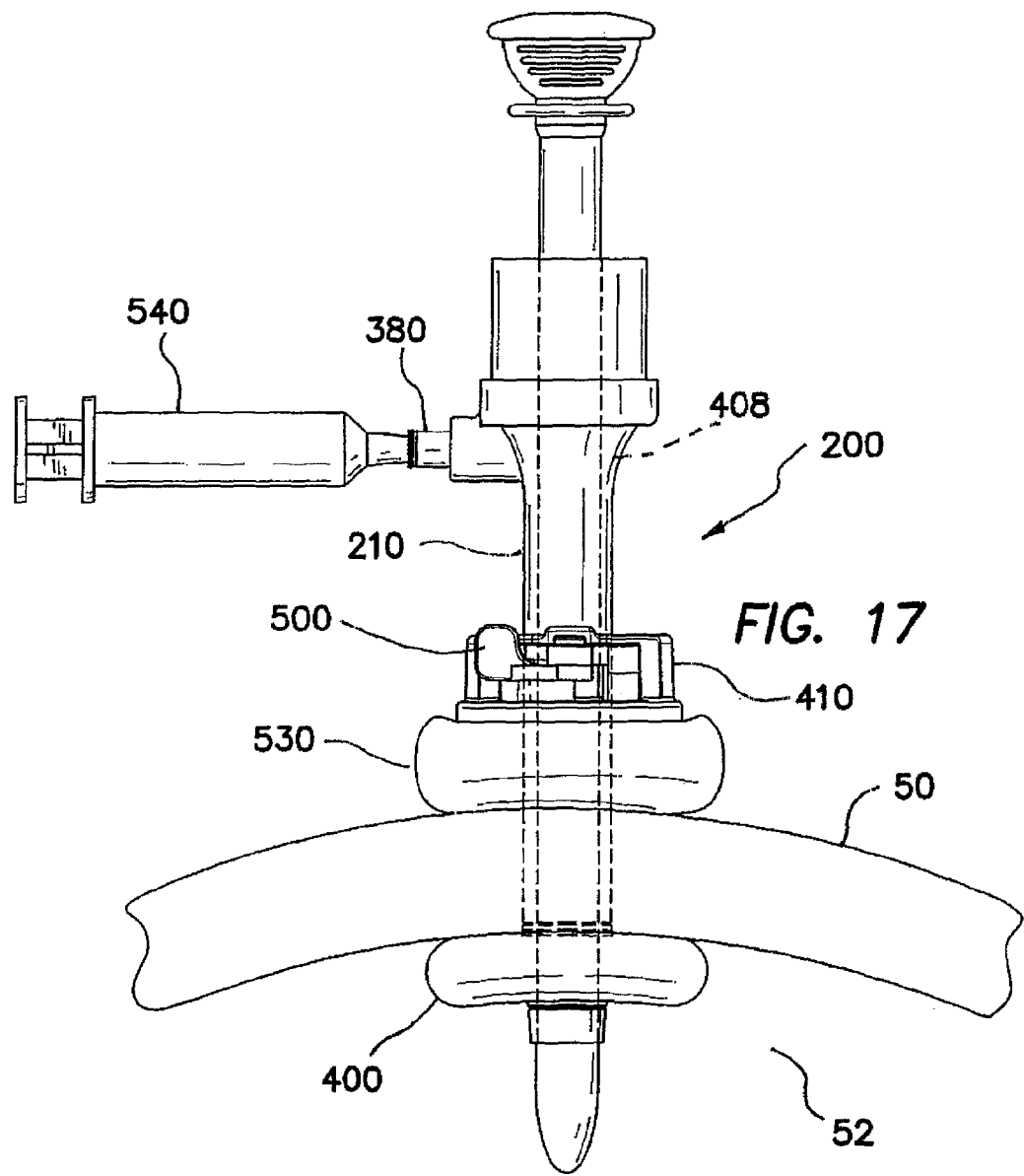
FIG. 17 illustrates a cannula assembly placed through a body wall.

Referring to FIG. 17, once an incision is made in the body wall 50 to gain entry to the body cavity 52, such as the abdominal cavity, the distal end of the balloon trocar 200 is inserted through the incision until the balloon 400 at the distal portion of the cannula assembly 210 is within the body cavity. A syringe 540 may be inserted into the port 380 and used to inflate the balloon 400 by injecting gas or fluid into the chamber 408. To seal the balloon 400 against the interior surface of the body wall 50, the bolster 410 may be advanced distally along the cannula while pulling the balloon trocar 200 proximally until the inflated balloon is compressed against the inner surface of the body wall 50 and the gel pad 530 is compressed against the outer surface of the body wall. The lever 500 may be rotated to apply clamping force from the clamp mechanism 415 onto the outer sleeve 300 to maintain the position of the bolster on the cannula assembly 210, thereby maintaining compression of the balloon 400 against the interior surface of the body wall 50 and compression of the gel pad 530 against the exterior surface of the body wall. With the incision sealed, the body cavity 52, such as the abdominal cavity, may be insufflated with $CO_2$ or a similar gas. To deflate the balloon 400 for removal of the balloon trocar 200 from the body cavity 52, the plunger 384 (see FIG. 18) within the port 380 may be depressed to release the gas or fluid from the balloon. The syringe 540 may be used to depress the plunger 384 within the port 380 and the syringe used to pull the gas or fluid from the chamber 408, thereby deflating the balloon 400.

Figure 29:
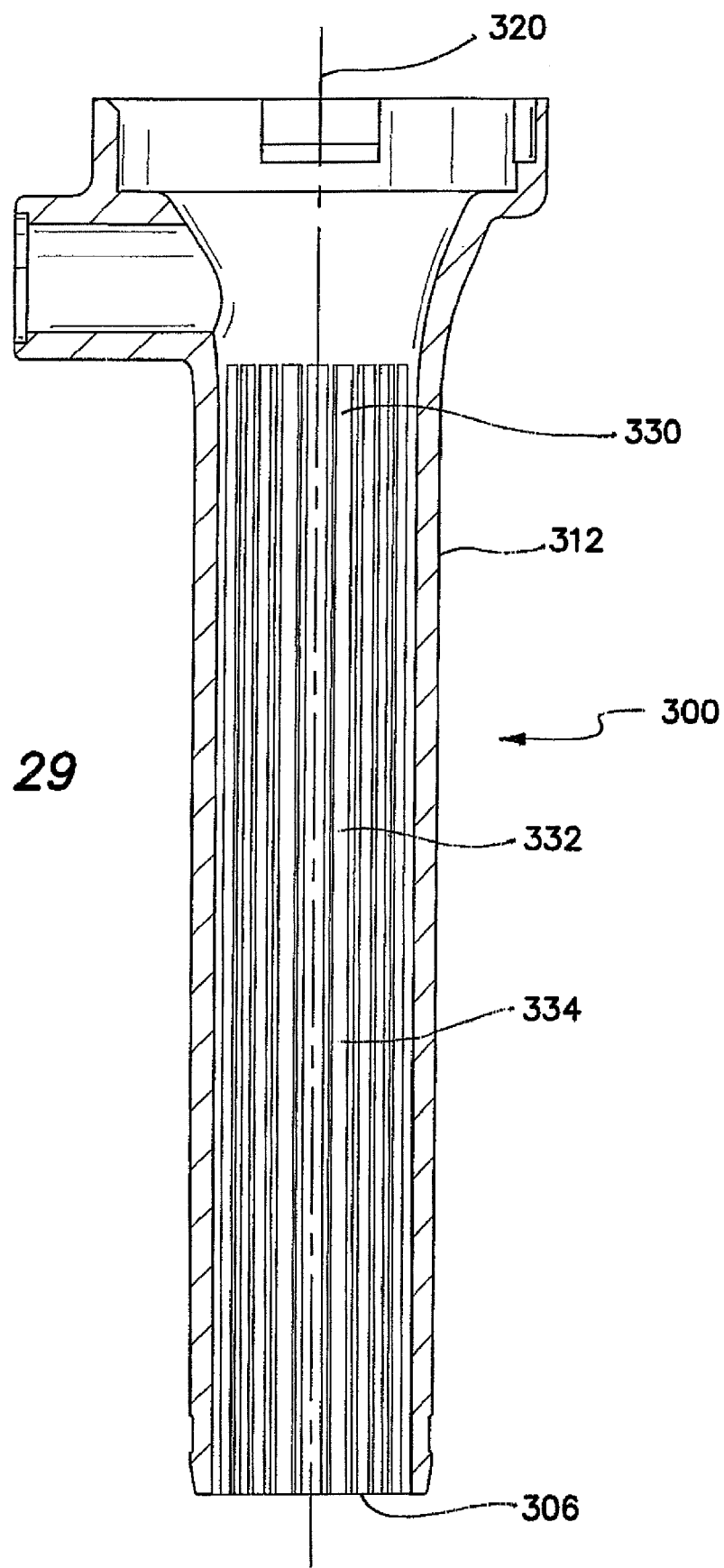
FIG. 29 is a plan view, in cross section of a sleeve portion of the balloon trocar of FIG. 13 with an inner surface of the sleeve including channels.
Figure 30:
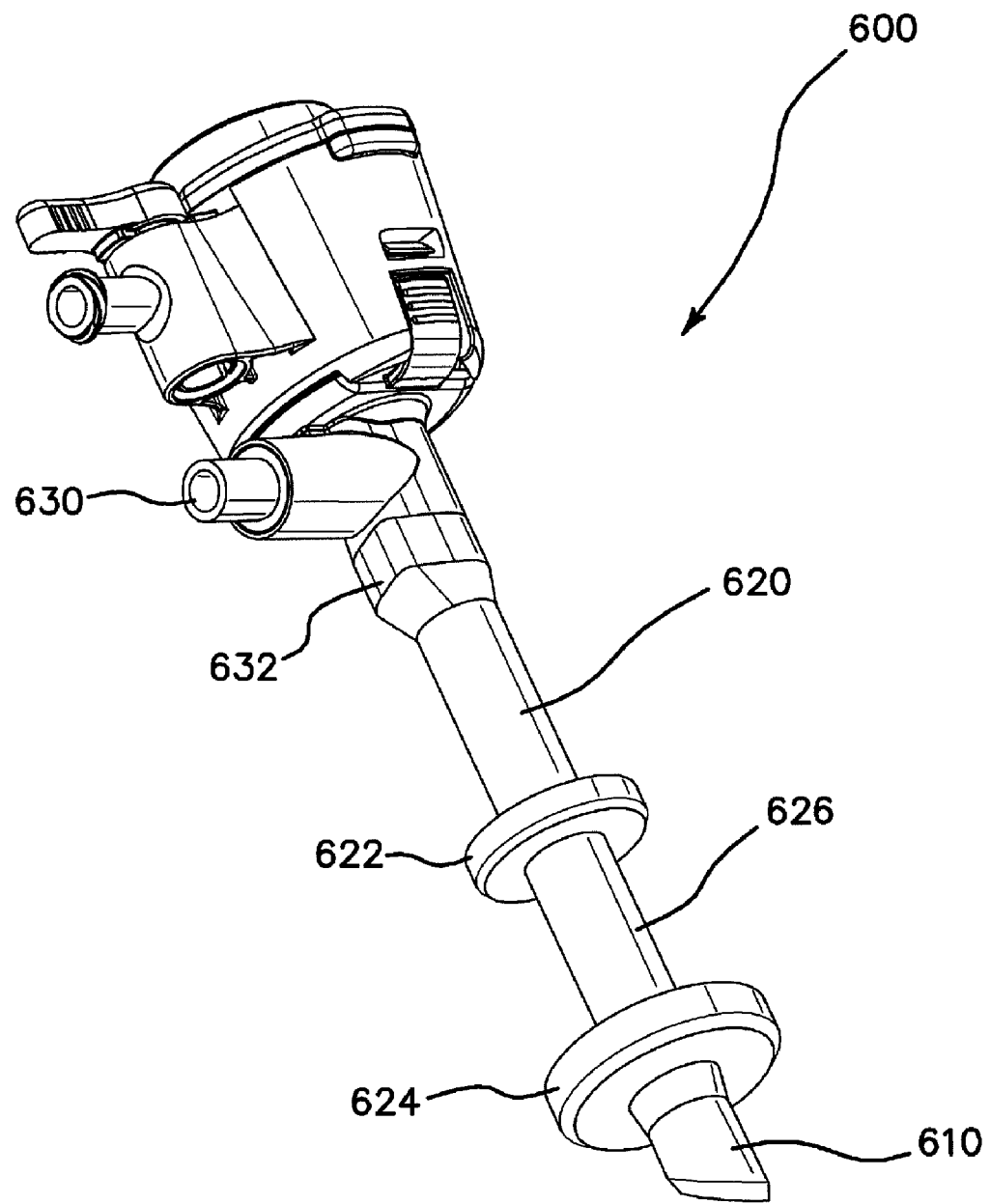
FIG. 30 is a perspective view of one embodiment of a cannula assembly including a retention mechanism for advanced fixation.
Figure 31:
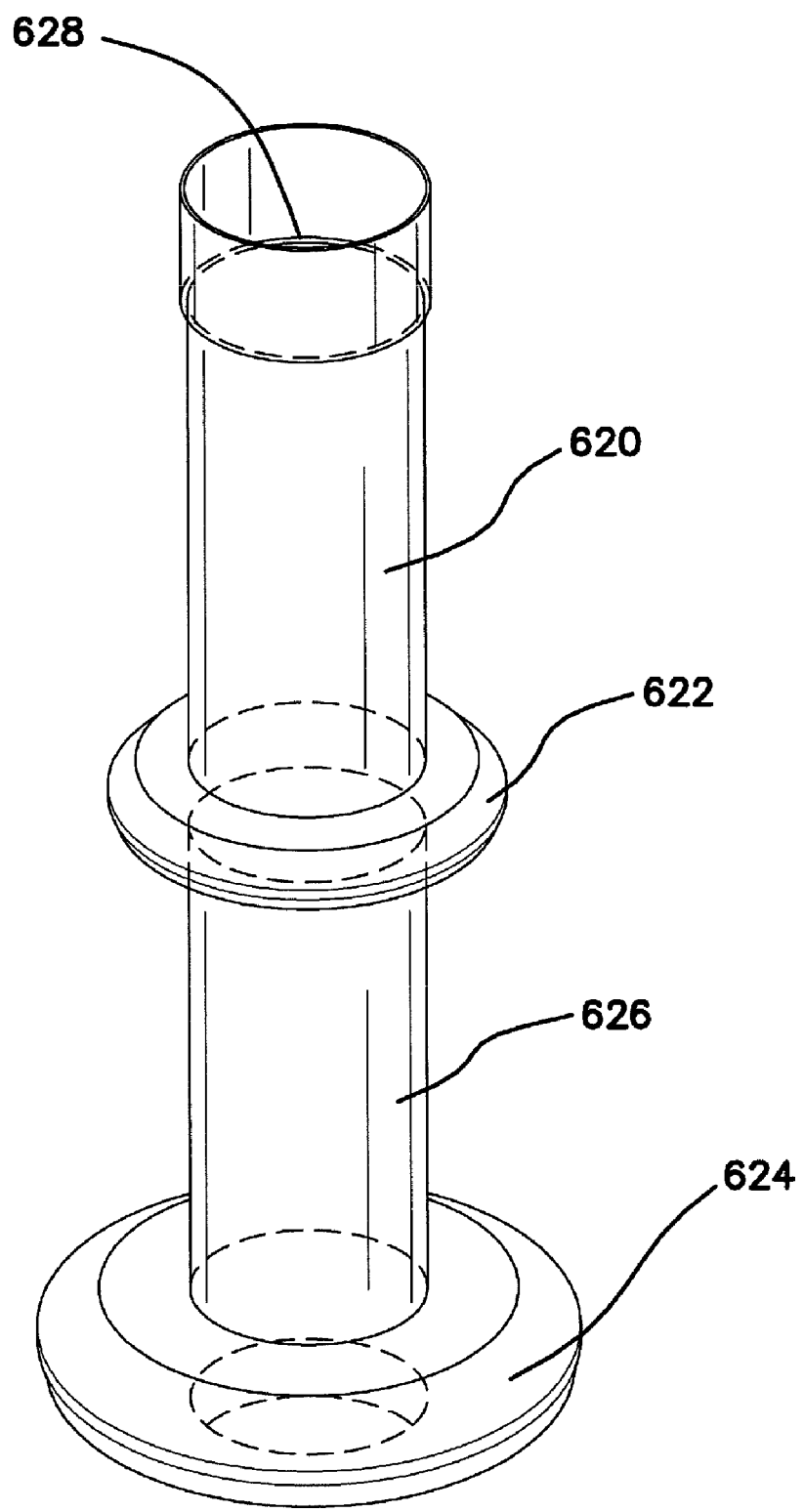
FIG. 31 is a perspective view illustrating the retention mechanism of the cannula assembly of FIG. 30.
Figure 32:
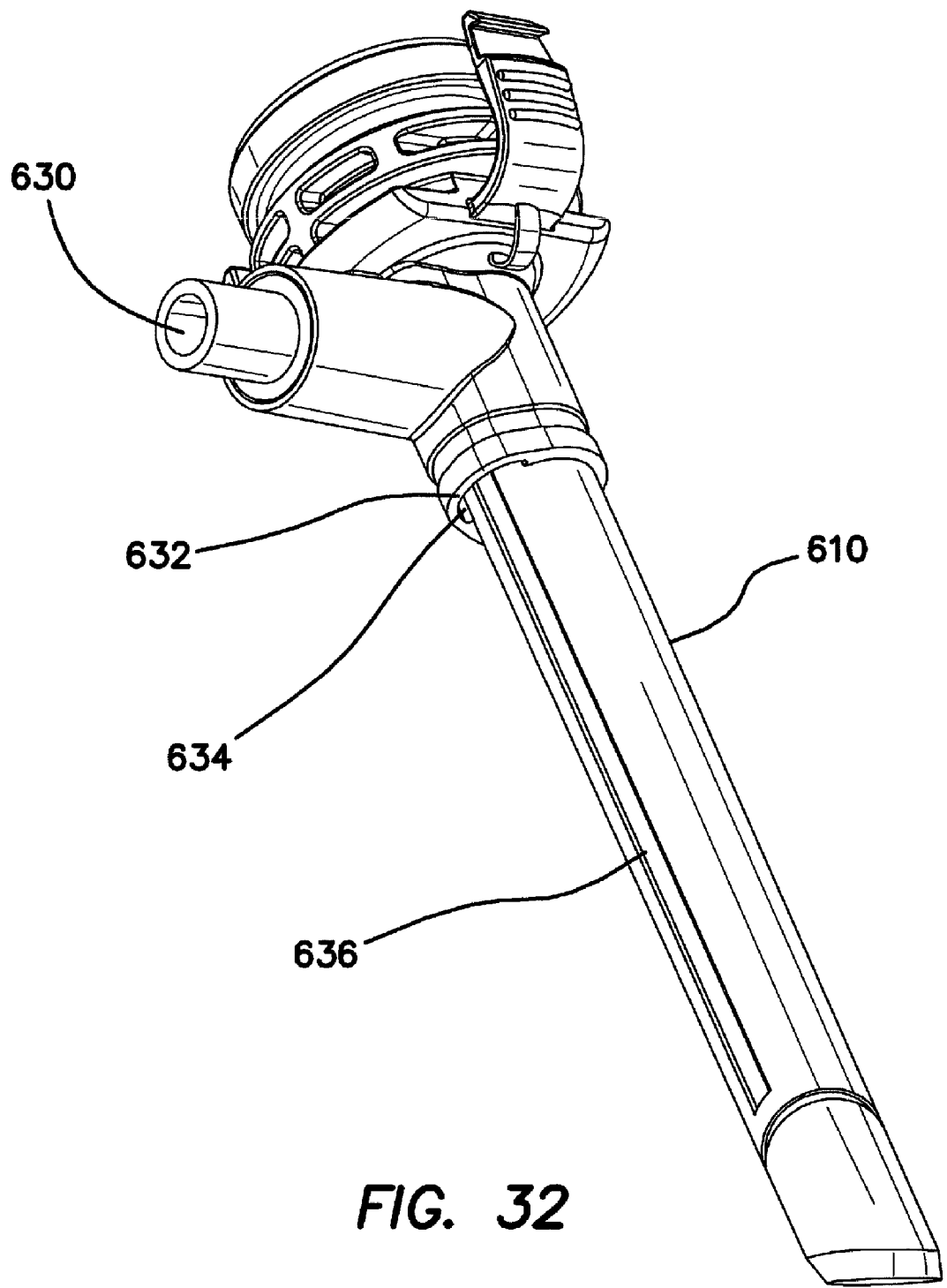
FIG. 32 is a perspective view illustrating a cannula of the cannula assembly of FIG. 30.
Figure 33:
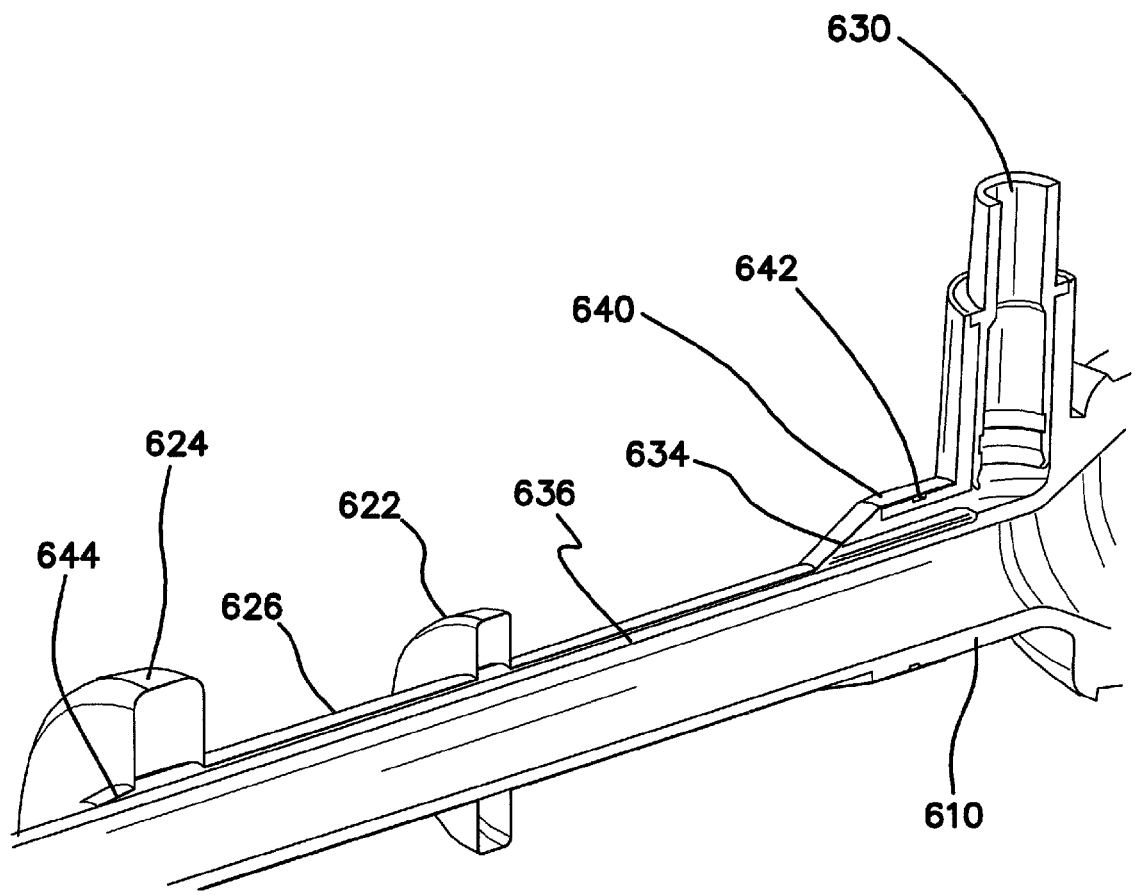
FIG. 33 is a longitudinal cross-sectional view of the cannula assembly of FIG. 30.
Figure 34:
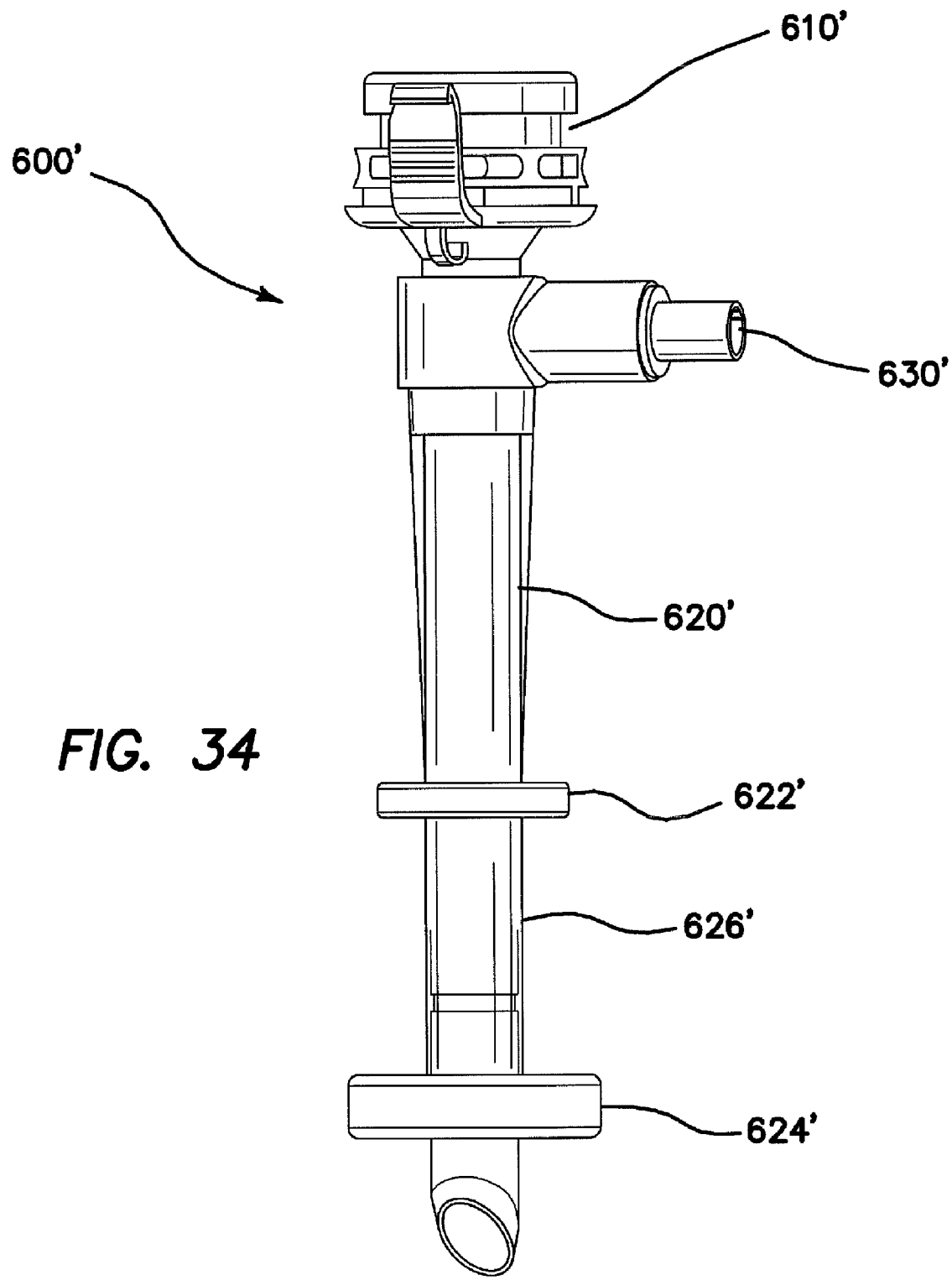
FIG. 34 is one embodiment of a cannula assembly having a cannula and a retention mechanism.
Figure 35:
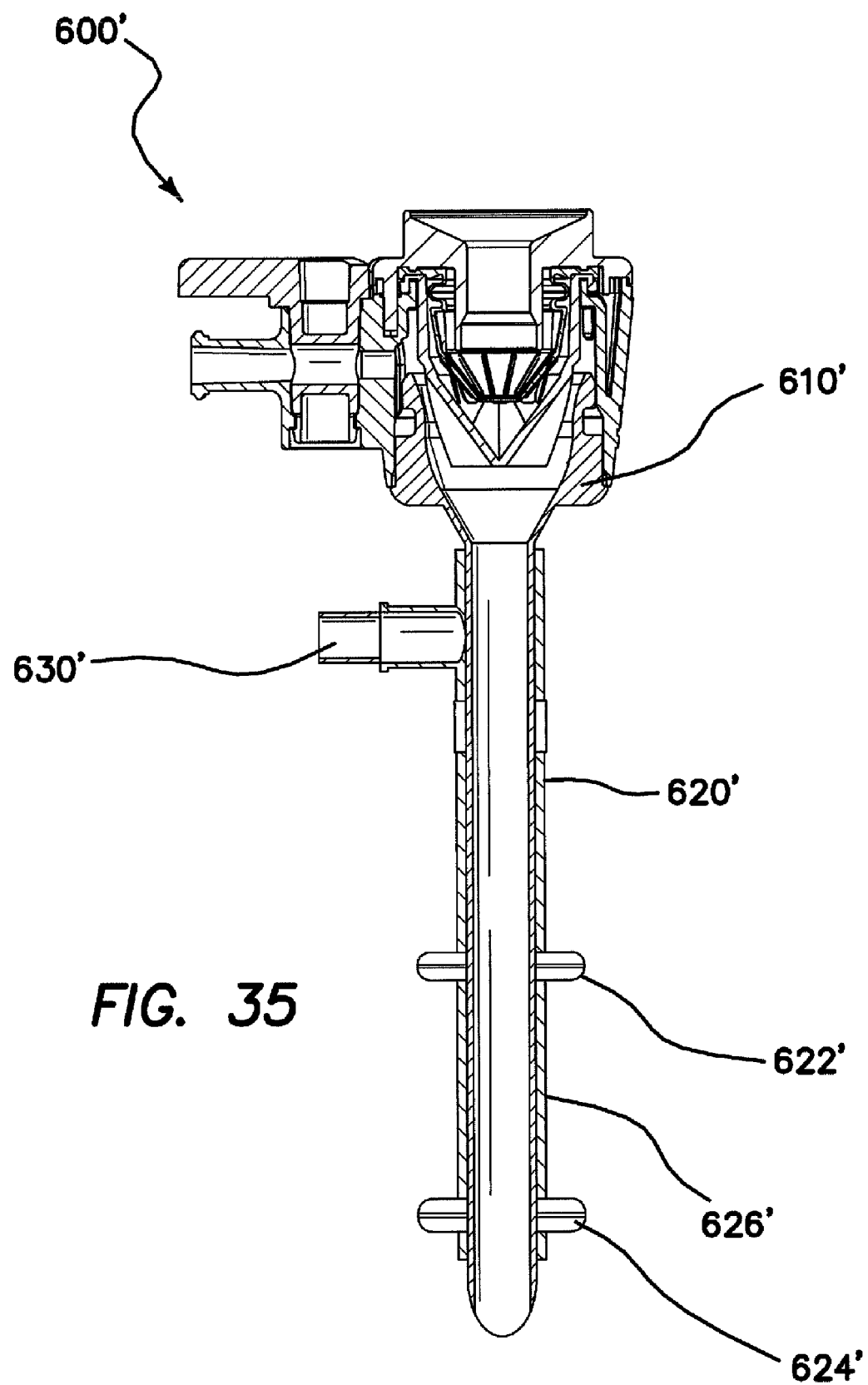
FIG. 35 is a longitudinal cross-sectional view of the cannula assembly of FIG. 34.

Referring to FIG. 29, an inner surface 330 of the outer sleeve 300 may include a plurality of channels 332 extending along the length of the outer sleeve from substantially the proximal end of the distal portion 312 of the outer sleeve distally to the distal end 306 of the outer sleeve. The channels 332 are similar to the channels 268 described for the outer surface of the cannula 250. The plurality of channels 332 on the inner surface 330 of the outer sleeve 300 is adapted to facilitate the flow of gases or fluids therethrough. In one aspect, the plurality of channels 332 on the inner surface 330 of the outer sleeve 300 may include a plurality of substantially longitudinal grooves 334 that are substantially parallel to the longitudinal axis 320 of the outer sleeve. With the plurality of channels 332 on the inner surface 330 of the sleeve 300, the sleeve 300 may be used with either the cannula 250 having a plurality of channels 268 on the outer surface of the cannula to further increase the flow of gases or fluids between the sleeve and cannula, or a cannula having a substantially smooth outer surface.

In FIGS. 30-41, various embodiments of a balloon trocar with advanced fixation are illustrated. FIGS. 30-33 relate to certain embodiments of a balloon trocar with advanced fixation having a cannula assembly that is integral with a balloon trocar retention mechanism. FIGS. 34-41 relate to certain embodiments of a balloon trocar with advanced fixation having a retention mechanism that can be selectively engaged with a trocar cannula.

With continued reference to FIGS. 30-41, the trocars of the illustrated embodiments can be used in general, abdominal, gynecological and thoracic minimally invasive surgical procedures to establish a path of entry or to gain access through the tissue planes and/or potential spaces for endoscopic instruments. In some embodiments, the trocar can comprise a trocar valve housing removably coupled to a cannula assembly 600, 600'. The valve housing in one aspect includes an inlet for supplying insufflation gas into the abdominal cavity. In the illustrated embodiments, the valve housing encloses an instrument seal and a zero seal, sealing an instrument channel path through the valve housing into the lumen of the cannula. While certain trocar assemblies are illustrated in conjunction with the retention mechanisms described and illustrated herein, it is contemplated that some or all of the aspects of the retention mechanisms described herein can be used in conjunction with other trocar assemblies.

Figure 36:
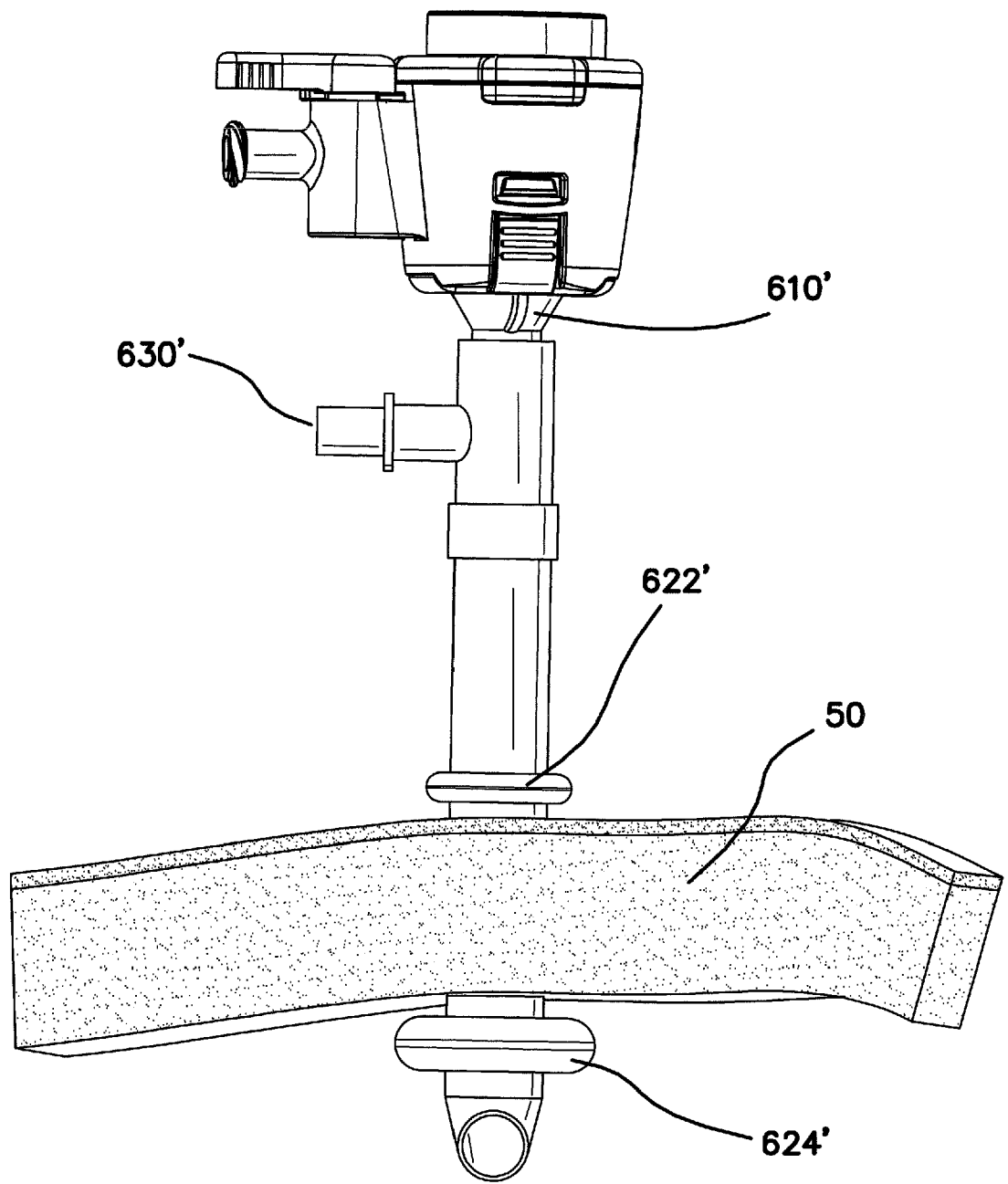
FIG. 36 is a perspective view of the cannula assembly of FIG. 34 placed through a body wall.
Figure 37:
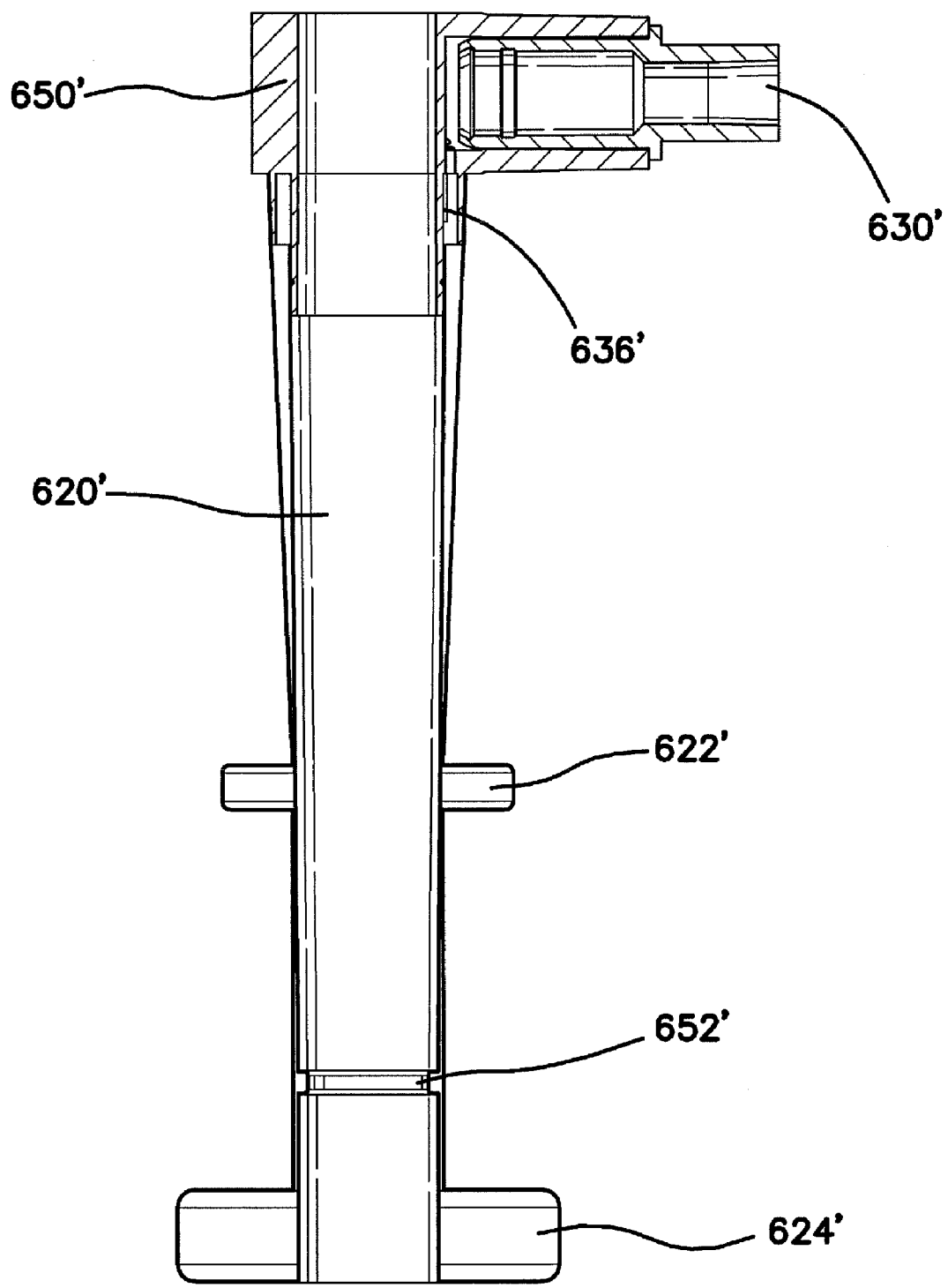
FIG. 37 is a longitudinal cross-sectional view of the retention mechanism of the cannula assembly of FIG. 34.

The cannula assembly 600, 600' further comprises a retention mechanism 620, 620' integrated with (FIGS. 30-33) or removably attached to (FIGS. 34-41) an outer surface of the cannula 610, 610'. The retention mechanism 620, 620' has a proximal end and a distal end. The retention mechanism 620, 620' comprises two inflatable balloons: a first inflatable balloon 624, 624' positioned near the distal end, and a second inflatable balloon 622, 622' positioned between the proximal end and the distal end. The first and second inflatable balloons 624, 624', 622, 622' can be spaced apart by a mid-section 626, 626' of an outer surface of the cannula 610, 610' configured to interface with a body wall 50 of a patient (FIG. 36).

With reference to FIGS. 30-33, in one aspect, the retention mechanism 620 is monolithically integral or otherwise attached to the trocar cannula 610. For example, the proximal and distal ends of the retention mechanism 620 can be adhered to the trocar cannula and/or secured with securing members such as winding threads, belts, bands, clips, or other suitable securing members. In the illustrated embodiment, winding threads are wound at each end to secure the balloons. As illustrated, the cannula 610 includes a proximal winding recess or groove 642, and a distal winding recess or groove formed therein. A proximal winding thread 640 can encircle the proximal end of the retention mechanism 620 and compress the retention mechanism 620 into the proximal groove 642 to maintain the retention mechanism 620 on the cannula 610. A distal winding thread 644 can encircle the distal end of the retention mechanism 620 and compress the retention mechanism 620 into the distal groove to maintain the retention mechanism 620 on the cannula 610. Certain aspects and advantages of a winding thread securement discussed herein with respect to other embodiments of balloon trocar are equally applicable to the winding thread securement of the retention mechanism 620 of FIGS. 30-33.

With continued reference to FIGS. 30-33, an inlet 630 at the proximal end of the retention mechanism 620 is in fluid communication with the two balloons 622, 624 through a fluid conduit. In some embodiments, a check valve positioned in the inlet 630 provides a port to introduce inflation fluid from a source of inflation fluid such as an air-filled syringe. In other embodiments, other valves or port configurations can be used to interface with a fluid source. In some embodiments, the cannula 610 can be formed with an inlet dome 632, which defines an inlet cavity 634 between an outer surface of the cannula 610 and the inlet dome 632. Advantageously, the inlet cavity 634 can be sized such that inflation fluid flowing in through the inlet 630 encounters relatively little resistance through the inlet cavity 634. The inlet cavity 634 can be fluidly coupled to one or more channels 636 or grooves formed in the outer surface of the cannula. As illustrated, the channels 636 extend generally parallel to the longitudinal axis of the cannula to provide a conduit for fluid to flow to the two balloons 622, 624. In the illustrated embodiments, inflation fluid can flow in the channels 636 between an outer surface of the cannula 610 and an inner surface 628 of the retention member 620. In other embodiments, channels formed in the cannula 610 can extend in a different orientation, such as, for example, transverse to the longitudinal axis of the cannula, curvilinearly or helically.

In one aspect, non-balloon portions of the retention mechanism 620, such as the mid-section 626 of the retention mechanism 620 and a section of the retention mechanism 620 proximal the second balloon 622, are strengthened or reinforced to resist pressure from the inflation fluid to aid in preventing stretching of the non-balloon portions. For example, in embodiments where the retention mechanism 620 is formed of a single material, the non-balloon sections of the retention mechanism 620 can be thicker than the two balloons 622, 624. In other embodiments, the retention mechanism 620 can be formed of a relatively non-inflatable material in the non-balloon portions and a relatively inflatable material in the two balloons 622, 624. Thus, the two balloons 622, 624 can inflate while the non-balloon portions remain substantially non-inflated when inflation fluid is supplied to the retention mechanism.

With respect to FIGS. 34-41, in certain embodiments, a retention mechanism 620' comprises a double layered inflatable member or balloon that is adapted to be removably attached to a trocar cannula 610' to form a cannula assembly 600'. As illustrated, an inlet housing 650' is attached to the proximal end of the inflatable member. In some embodiments, the inlet housing 650' comprises an inlet 630' coupled to an annular member. The annular member comprises a central opening therein configured to receive a cannula 610' therethrough. In some embodiments, the inlet 630' comprises a check valve integrated therewith to receive a supply of inflation fluid such as air from a fluid source such as a syringe. In other embodiments, other valves or port configurations can be used to interface with a fluid source.

With continued reference to FIGS. 34-41, the retention mechanism 620' comprises a fluid conduit fluidly coupling the inlet 630' to the inflatable member. In some embodiments, the inlet housing 650' can comprise one or more fluid channels 636' (FIG. 37) formed therein fluidly coupling the inlet 630' to the inflatable member.

With continued reference to FIGS. 34-41, the inflatable member can comprise an inner layer, an outer layer, and a fluid chamber formed between the inner layer and the outer layer. In some embodiments, the inner layer can be generally cylindrical and adapted to receive a cannula 610' therein. The outer layer can comprise the first inflatable balloon 624' and the second inflatable balloon 622' formed thereon. As discussed above, the fluid chamber can be fluidly coupled to the inlet 630' via one or more fluid channels 636' in the inlet housing 650'

Figure 40:
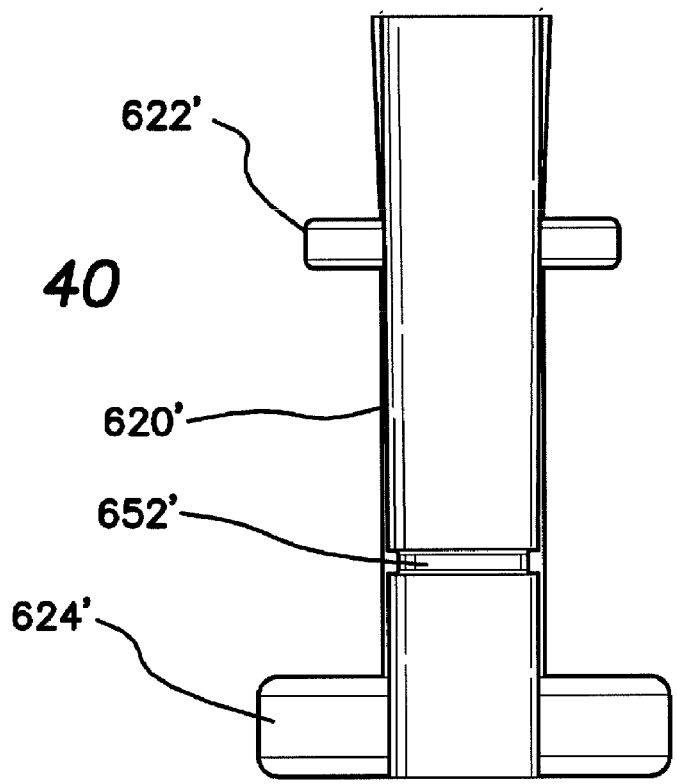
FIG. 40 is a longitudinal cross-sectional view of a distal end of the retention mechanism of the cannula assembly of FIG. 34.
Figure 41:
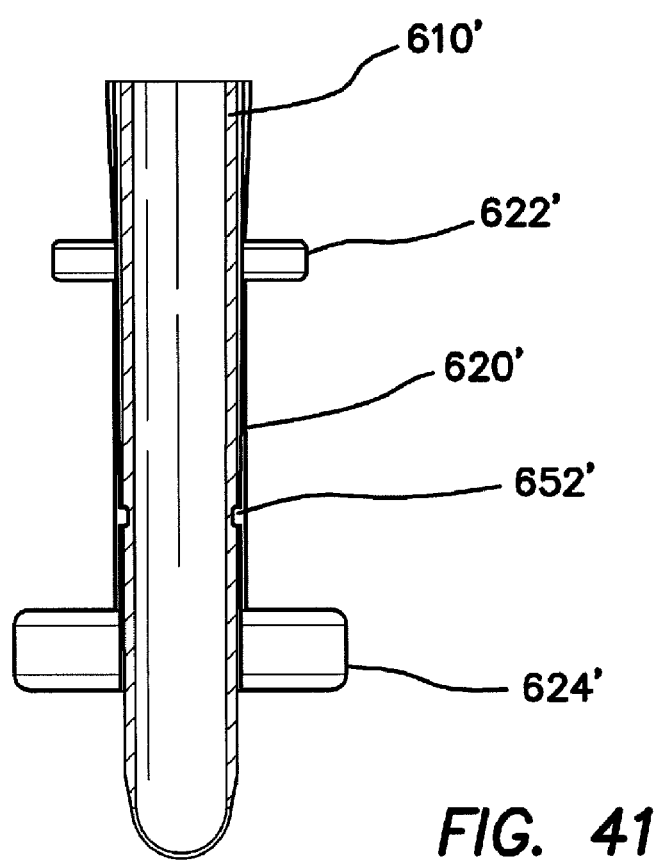
FIG. 41 is a longitudinal cross-sectional view of a distal end of the retention mechanism of the cannula assembly of FIG. 34 with a cannula inserted therein.

The retention mechanism 620' can be configured to selectively maintain the position of the retention mechanism 620' on the cannula 610'. An inflation fluid can be introduced between the layers in the layered balloon, such that the inner layer, the layer to be placed against or adjacent to the outer surface of the cannula, is further secured against the cannula by pressure from the injected fluid. In one aspect, a recess, a projection, a catch, or another suitable interface feature is provided on the outer wall or surface of the cannula 610'. As such, the inner layer of the inflatable member injected with inflation fluid forms against the interface feature to further secure the retention mechanism 620' to the cannula. In one aspect, a detent, projection, a micro inner balloon 652', or another suitable cannula retention feature formed on the inner layer of the inflatable member can be provided to act as a key to position the retention mechanism 620' to the cannula 610' and to provide a seal between the retention mechanism 620' and the cannula 610', and/or to secure the retention mechanism 620' to the outer surface of the cannula 610'. In one aspect, the projection or inner balloon 652' is sized and configured to fill a corresponding interface feature such as a space or indent on the outer surface of the cannula 610' when the inflatable member is injected with inflation fluid to seal and/or secure the retention mechanism 620' against the cannula 610'. FIGS. 40-41 illustrate retention of a cannula 610 by an inner balloon 652' of the retention mechanism 620'.

Figure 38:
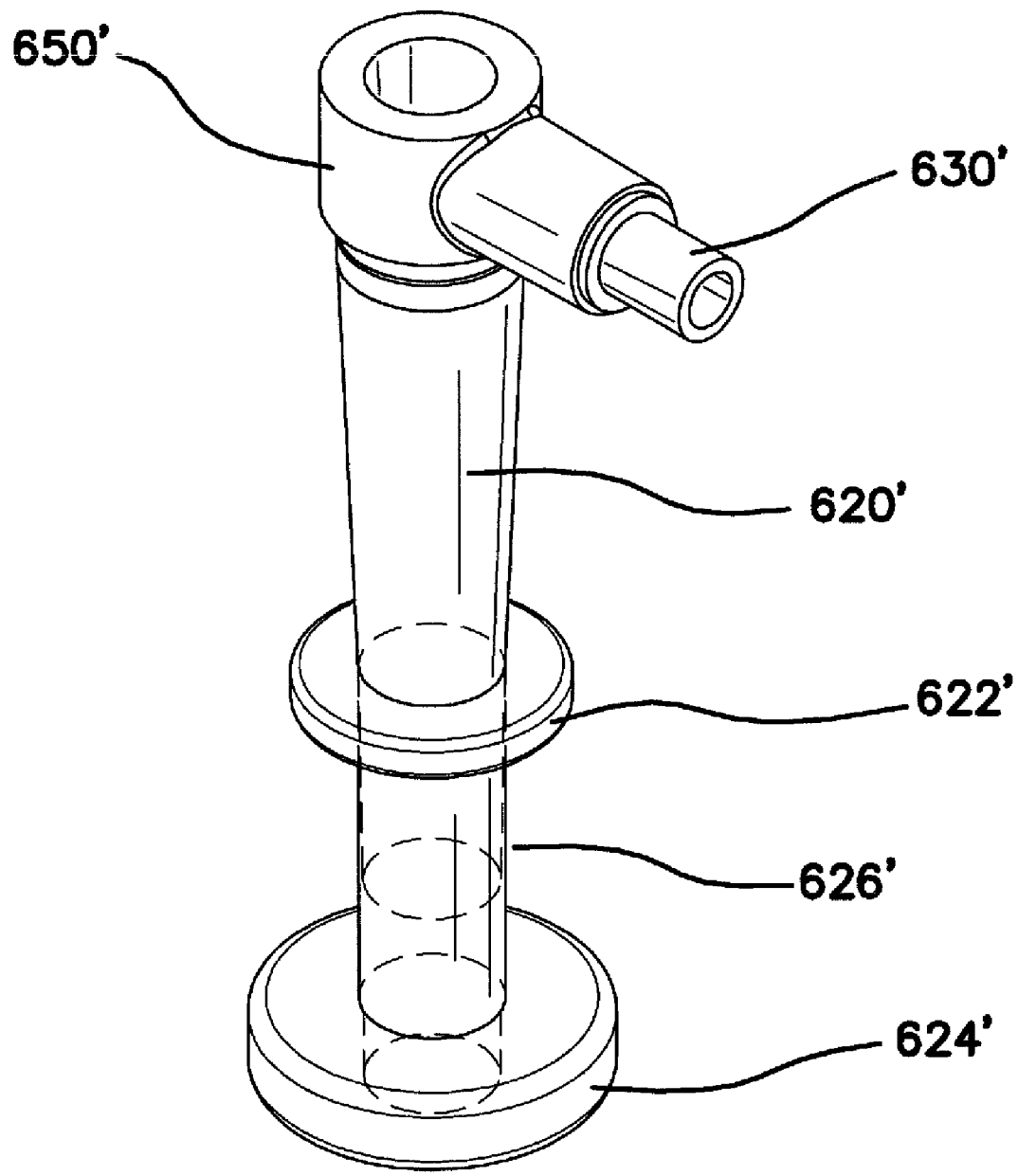
FIG. 38 is a partial cross-sectional view of the retention mechanism of the cannula assembly of FIG. 34.
Figure 39:
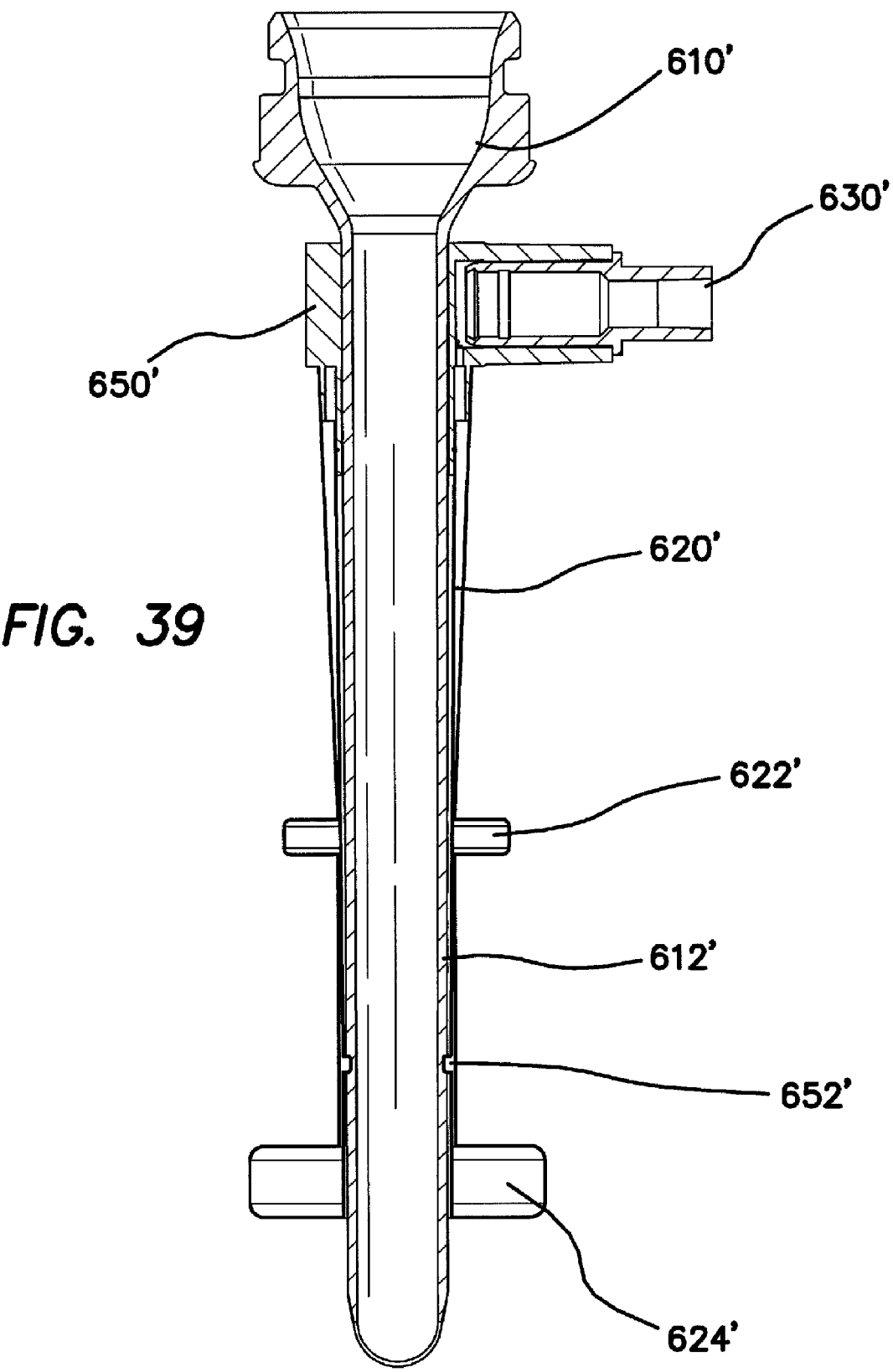
FIG. 39 is a longitudinal cross-sectional view of the cannula assembly of FIG. 34.

In certain embodiments, additional balloons can be incorporated on the retention mechanism to account for variations in a patient's abdominal wall thickness and anatomy. In certain embodiments, the balloons 622, 622', 624, 624' can be distensible or non-distensible or a combination of both. In certain embodiments, the balloons 622, 622', 624, 624' are annular and can be toroidal or doughnut shaped (FIGS. 35-36) or in certain other embodiments disc-like (FIGS. 38-39). In other embodiments, the balloons can have other geometries. In certain embodiments, the proximal balloon 622, 622' can differ in size, e.g., smaller inflated volume, and/or shape, e.g., flatter, as compared to the distal balloon 624, 624'. In other embodiments, the balloons 622, 622', 624, 624' can have substantially the same size and shape. The size and/or location of the balloons 622, 622', 624, 624' can varied from that of the illustrated embodiments to vary the desired retention characteristics of the cannula assemblies 600, 600' to correspond to a patient's body. For example, in certain embodiments the distal balloon 624, 624' and/or the proximal or mid-point balloon 622, 622' can be positioned to be inflated within portions of the abdominal wall. In certain embodiments, the balloons 622, 622', 624, 624' can be comprised of one of silicone, polyisoprene, urethane, polyolefin, and Mylar, or a mixture of more than one thereof. In some embodiments, the balloons 622, 622', 624, 624' can include a layer of a grease or another sealing element disposed therein, as described above with respect to certain embodiments of balloon. In some embodiments, the first balloon 624, 624' can comprise a different material than that of the second balloon 622, 622'.

In certain embodiments, methods for securing a cannula assembly having a retention mechanism 620, 620' such as one of the various embodiments discussed above for a laparoscopic procedure is provided. A surgeon can make an incision to gain entry to the abdominal or thoracic cavity. In embodiments having removably attachable retention mechanisms, such as those of FIGS. 34-41, the surgeon can slidably advance the retention mechanism 620' about the cannula 610' to form a cannula assembly 600'. The surgeon can then insert the cannula assembly 600, 600' through the incision until the balloon 624, 624' mounted on the distal tip of the cannula is within the cavity and the second balloon 622, 622' at or near the middle of the cannula is outside of the peritoneal lining. At this point, the balloons are inflated. In certain embodiments, the surgeon can use a syringe removably coupled to an inlet 630, 630' attached to the cannula assembly 600, 600', to supply inflation fluid such as air into the balloons 622, 622', 624, 624'. This inflation of the balloons 622, 622', 624, 624' secures the cannula assembly 600, 600' to the abdominal or thoracic wall, reducing displacement of the cannula assembly 600, 600' during the surgery and/or instrument removal.

The inflated balloon 624, 624' at the distal end of the retention mechanism 620, 620' reduces the risk that the cannula assembly 600, 600' would be pulled out when an instrument is removed from the cannula 610, 610'. The inflated second balloon 622, 622' reduces the risk that the cannula assembly 600, 600' would be pushed further into the patient during surgery. Together, these two balloons 622, 622', 624, 624' reduce the risk of dislodging motion of the cannula assembly 600, 600' during surgery. In certain embodiments, to deflate the balloons, the syringe is pushed into the check valve. The inflation pressure inside the balloons can then push the syringe's piston back. Additional user manipulation, e.g., pulling the piston back, can cause the balloons 622, 622', 624, 624' to completely deflate.

Although the present inventions have been described in certain specific aspects, many additional modifications and variations would be apparent to those skilled in the art. It is therefore to be understood that the present inventions may be practiced otherwise than specifically described, including various changes in the size, shape and materials, without departing from the scope and spirit of the present invention. Thus, embodiments of the present inventions should be considered in all respects as illustrative and not restrictive.

What is claimed is:

1. A cannula assembly comprising:
    a cannula having a proximal end, a distal end, an outer surface, a proximal groove in the outer surface at the proximal end, and a distal groove in the outer surface at the distal end, and a lumen extending between the proximal end and the distal end, the lumen adapted to receive a medical instrument therein;
    a retention mechanism attached to the outer surface of the cannula and having a proximal end secured to the proximal groove of the cannula and a distal end secured to the distal groove of the cannula, the retention mechanism comprising:
        a first inflatable balloon positioned near the distal end of the retention mechanism;
        a second inflatable balloon positioned between the proximal end and the distal end of the retention mechanism; and
        a mid-section extending between the first inflatable balloon and the second inflatable balloon, the mid-section having an outer surface adapted to contact a body wall of a patient when in use;
    an inlet monolithically integrally formed with the cannula near the proximal end of the retention mechanism, the inlet in fluid communication with the first and second balloons and the mid-section of the retention mechanism; and
    a fluid conduit fluidly coupling the inlet with the first and second inflatable balloons; and
    wherein the mid-section is configured such that upon application of an inflation fluid to the inlet, the first and second balloons inflate before the mid-section.

2. The cannula assembly of claim 1, wherein at least one of the first and second balloons comprises a toroidal profile.

3. The cannula assembly of claim 2, wherein both of the first and second balloons comprise a toroidal profile.

4. The cannula assembly of claim 1, wherein at least one of the first and second balloons comprises a disc profile.

5. The cannula assembly of claim 4, wherein both of the first and second balloons comprise a disc profile.

6. The cannula assembly of claim 1, wherein the fluid conduit comprises:
    an air inlet cavity fluidly coupled to the inlet; and
    a fluid channel extending generally longitudinally along the outer surface of the cannula.

7. The cannula assembly of claim 1, wherein the retention mechanism is attached to the cannula by a proximal thread winding at the proximal end of the retention mechanism and a distal thread winding at the distal end of the retention mechanism.

8. A retention mechanism for a cannula assembly, the retention mechanism comprising:
    an inlet housing comprising:
        an annular member having an opening adapted to receive the cannula assembly; and
        an inlet port adapted to receive a source of inflation fluid; and
    an inflatable member having a proximal end and a distal end, the proximal end of the inflatable member fluidly coupled to the inlet port of the inlet housing, and the inflatable member comprising:
   an inner layer defining a generally cylindrical surface adapted to receive the cannula assembly therein;
   an outer layer comprising:
      a first inflatable projection positioned near the distal end of the inflatable member; and
      a second inflatable projection positioned between the proximal end and the distal end of the inflatable member and spaced apart from the first inflatable projection; and
   a fluid chamber formed between the inner layer and the outer layer, the fluid chamber being fluidly coupled to the inlet port.

9. The retention mechanism of claim 8, wherein the inner layer of the inflatable member comprises a retention feature extending radially inwardly therefrom and configured to retain the cannula assembly.

10. The retention mechanism of claim 9, wherein the retention feature comprises an inflatable balloon.

11. The retention mechanism of claim 8, wherein the first inflatable projection and the second inflatable projections each comprise an inflatable balloon.

12. The retention mechanism of claim 8, wherein the inflatable projection and the second inflatable projections each define a generally annular structure in an inflated state.

13. The retention mechanism of claim 8, wherein the inlet port of the inlet housing is coupled to the annular member, and the annular member comprises fluid conduits fluidly coupled to the inlet port and fluidly coupled to the inflatable member.

14. The retention mechanism of claim 8, wherein the inlet housing comprises a rigid material.

15. A cannula assembly comprising:
   a cannula having a proximal end, a distal end, an outer surface, and a lumen extending between the proximal end and the distal end, the lumen adapted to receive a medical instrument therein, the cannula comprising:
      an inlet port monolithically integrally formed with the cannula on the outer surface of the cannula; and
      a fluid conduit extending generally longitudinally in the outer surface of the cannula, the fluid conduit fluidly coupled to the inlet port; and
      an inlet dome formed on the outer surface of the cannula, the inlet dome defining an inlet chamber between the outer surface of the cannula and the inlet dome, the inlet dome fluidly coupled to the inlet port and the fluid conduit; and
   a retention mechanism coupled to the outer surface of the cannula and having a proximal end and a distal end, the retention mechanism comprising:
      a first inflatable balloon positioned near the distal end of the retention mechanism; and
      a second inflatable balloon positioned between the proximal end and the distal end of the retention mechanism; and
      wherein the first and second inflatable balloons are fluidly coupled to the fluid conduit on the cannula.

16. The cannula assembly of claim 15, wherein the inlet port comprises a check valve positioned therein, the check valve adapted to receive a syringe of fluid.

17. The cannula assembly of claim 15, wherein the cannula further comprises a proximal groove and a distal groove and wherein the retention mechanism further comprises a proximal thread winding at the proximal end of the retention mechanism and a distal thread winding at the distal end of the retention mechanism, the proximal thread winding coupling the retention mechanism to the proximal groove, and the distal thread winding coupling the retention mechanism to the distal groove.

18. The cannula assembly of claim 15, wherein the first and second inflatable balloons each comprise a generally annular balloon.

19. The cannula assembly of claim 15, wherein the second inflatable balloon has a smaller inflated volume than the first inflatable balloon.

20. A method of securing a cannula assembly for a laparoscopic procedure on a patient comprising:
   providing a cannula assembly comprising:
      a cannula having a proximal end, a distal end, an outer surface, and a lumen extending between the proximal end and the distal end, the lumen adapted to receive a medical instrument therein;
      a retention mechanism attached to the outer surface of the cannula and having a proximal end and a distal end, the retention mechanism comprising:
         a first inflatable balloon positioned near the distal end of the retention mechanism; and
         a second inflatable balloon positioned between the proximal end and the distal end of the retention mechanism; and
         a mid-section extending between the first inflatable balloon and the second inflatable balloon, the mid-section having an outer surface adapted to contact a body wall of a patient when in use;
      an inlet monolithically integrally formed with the cannula near the proximal end of the retention mechanism, the inlet in fluid communication with the first and second balloons and the mid-section of the retention mechanism;
      a fluid conduit fluidly coupling the inlet with the first and second inflatable balloons; and
      an inlet dome formed on the outer surface of the cannula, the inlet dome defining an inlet chamber between the outer surface of the cannula and the inlet dome, the inlet dome fluidly coupled to the inlet and the fluid conduit; and
      wherein the mid-section is configured such that upon application of an inflation fluid to the inlet, the first and second balloons inflate before the mid-section;
   inserting the cannula assembly into an incision in the patient until the first inflatable balloon is positioned in a body cavity of the patient and the second inflatable balloon is outside of the incision of the patient; and
   inflating the first and second inflatable balloons.

21. The method of claim 20, wherein inflating the first and second inflatable balloons comprises introducing a source of inflation fluid to the inlet of the cannula assembly.

22. The method of claim 21, wherein the source of inflation fluid comprises a syringe of air.

* * * * *